United States Patent
Kurita et al.

(10) Patent No.: US 12,361,573 B2
(45) Date of Patent: Jul. 15, 2025

(54) INFORMATION PROCESSING APPARATUS AND INFORMATION PROCESSING METHOD FOR SHAPE MEASUREMENT OF TARGET

(71) Applicant: SONY GROUP CORPORATION, Tokyo (JP)

(72) Inventors: Teppei Kurita, Tokyo (JP); Shinichiro Gomi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 302 days.

(21) Appl. No.: 17/755,725

(22) PCT Filed: Nov. 9, 2020

(86) PCT No.: PCT/JP2020/041676
§ 371 (c)(1),
(2) Date: May 6, 2022

(87) PCT Pub. No.: WO2021/095672
PCT Pub. Date: May 20, 2021

(65) Prior Publication Data
US 2023/0044097 A1    Feb. 9, 2023

(30) Foreign Application Priority Data

Nov. 15, 2019    (JP) .................................. 2019-207103

(51) Int. Cl.
*G06T 7/50*    (2017.01)
*G06T 5/70*    (2024.01)
(Continued)

(52) U.S. Cl.
CPC .................. *G06T 7/50* (2017.01); *G06T 5/70* (2024.01); *G06T 7/11* (2017.01); *G06V 10/141* (2022.01);
(Continued)

(58) Field of Classification Search
CPC ..... G06T 7/50; G06T 5/70; G06T 7/11; G06T 2207/10056; G06V 10/141; G06V 10/25;
(Continued)

(56) References Cited

U.S. PATENT DOCUMENTS 9,323,037 B2 *   4/2016   Yoshioka .................. G06T 7/70
10,083,371 B2 *   9/2018   Ebata ...................... G06T 7/001
(Continued)

FOREIGN PATENT DOCUMENTS

CN        101356546 A      1/2009
CN        107003115 A      8/2017
(Continued)

*Primary Examiner* — Mia M Thomas
(74) *Attorney, Agent, or Firm* — CHIP LAW GROUP

(57) ABSTRACT

Provided is an information processing device that includes a control unit. The control unit acquires a captured image of a target imaged by a sensor. The captured image is an image obtained from reflected light of light emitted to the target from a plurality of light sources arranged at different positions, respectively. The control unit extracts a flat region from the captured image based on a luminance value of the captured image. The control unit calculates shape information regarding a shape of a surface of the target based on information regarding the sensor and the flat region of the captured image.

13 Claims, 23 Drawing Sheets

(51) Int. Cl.
*G06T 7/11* (2017.01)
*G06V 10/141* (2022.01)
*G06V 10/25* (2022.01)
*G06V 10/60* (2022.01)
*G06V 10/74* (2022.01)

(52) U.S. Cl.
CPC .............. *G06V 10/25* (2022.01); *G06V 10/60* (2022.01); *G06V 10/761* (2022.01); *G06T 2207/10056* (2013.01)

(58) Field of Classification Search
CPC .. G06V 10/60; G06V 10/761; G06V 2201/03; G06V 20/69; G06V 10/82; A61B 5/107; G01B 11/24; G01B 11/30; G01N 21/27
See application file for complete search history.

(56) References Cited

U.S. PATENT DOCUMENTS

| | | | |
|---|---|---|---|
| 11,651,505 B2* | 5/2023 | Kempf | H04N 13/218 |
| | | | 348/48 |
| 2008/0186390 A1 | 8/2008 | Sato et al. | |
| 2014/0118502 A1* | 5/2014 | Jang | G06T 7/586 |
| | | | 348/46 |
| 2014/0168382 A1* | 6/2014 | Jang | G01B 11/2509 |
| | | | 348/46 |
| 2017/0243052 A1* | 8/2017 | Sugama | G06F 3/0425 |
| 2017/0276476 A1 | 9/2017 | Konno | |
| 2019/0244408 A1* | 8/2019 | Nishi | G06T 3/20 |
| 2020/0013819 A1 | 1/2020 | Toda | |
| 2020/0058111 A1* | 2/2020 | Wang | H04N 9/67 |
| 2020/0320682 A1* | 10/2020 | Alexander | G06F 18/2321 |
| 2020/0349684 A1* | 11/2020 | Jung | G06T 5/50 |

FOREIGN PATENT DOCUMENTS

| | | |
|---|---|---|
| JP | H10307011 A | 11/1998 |
| JP | 10-333057 A | 12/1998 |
| JP | 2008-253498 A | 10/2008 |
| JP | 2018200328 A | 12/2018 |
| JP | 2019-139694 A | 8/2019 |
| WO | 2007/139067 A1 | 12/2007 |
| WO | 2018/159738 A1 | 9/2018 |
| WO | WO-2019139694 A | 7/2019 |

* cited by examiner

| | SURFACE SHAPE | ASSUMP-TION 1 | ASSUMP-TION 2 |
|---|---|---|---|
| (1) | | ○ | ○ |
| (2) | | △ | ○ |
| (3) | | ✕ | ✕ |
| (4) | | ✕ | ✕ |

☐ BLOCK WHOSE CONTRAST VALUE IS EQUAL TO OR MORE THAN THRESHOLD
┌─┐ BLOCK WHOSE CONTRAST VALUE IS
└─┘ LESS THAN THRESHOLD

INFORMATION PROCESSING APPARATUS AND INFORMATION PROCESSING METHOD FOR SHAPE MEASUREMENT OF TARGET

CROSS REFERENCE TO RELATED APPLICATIONS

This application is a U.S. National Phase of International Patent Application No. PCT/JP2020/041676 filed on Nov. 9, 2020, which claims priority benefit of Japanese Patent Application No. JP 2019-207103 filed in the Japan Patent Office on Nov. 15, 2019. Each of the above-referenced applications is hereby incorporated herein by reference in its entirety.

FIELD

The present disclosure relates to an information processing device and an information processing method.

BACKGROUND

A microscope whose introduction cost is relatively low and which can easily perform measurement has been widely used as a device for observing a minute form of an object.

A technology for analyzing a color and stain of a skin surface by using a difference in incident angle of an illumination unit (for example, Patent Literature 1) has been known as a technology related to a microscope. In addition, a technology for reducing defocus and distortion at the time of capturing an image of a skin surface by arranging transparent glass at a predetermined distance from a distal end dome of a microscope has been known (for example, Patent Literature 2).

CITATION LIST

Patent Literature

Patent Literature 1: JP H10-333057 A
Patent Literature 2: JP 2008-253498 A

SUMMARY

Technical Problem

According to the conventional technology, quality of an image captured by a microscope can be improved.

However, the conventional technology merely improves quality of a planar image, and it is difficult to obtain a 3D image in which a minute shape (unevenness) of an object is reproduced. Note that a non-contact 3D measuring instrument, a 3D scanner, or the like is used as a device for measuring a minute shape of an object, but when these devices are introduced, there is a problem that the cost becomes relatively high. Note that a distance measurement device using a time of flight (ToF) method is relatively inexpensive, but may be insufficient in accuracy.

Therefore, the present disclosure provides an information processing device and an information processing method capable of improving accuracy in shape measurement.

Solution to Problem

According to the present disclosure, an information processing apparatus is provided. The information processing device includes a control unit. The control unit acquires a captured image of a target imaged by a sensor. The captured image is an image obtained from reflected light of light emitted to the target from a plurality of light sources arranged at different positions, respectively. The control unit extracts a flat region from the captured image based on a luminance value of the captured image. The control unit calculates shape information regarding a shape of a surface of the target based on information regarding the sensor and the flat region of the captured image.

DESCRIPTION OF EMBODIMENTS

Hereinafter, preferred embodiments of the present disclosure will be described in detail with reference to the appended drawings. Note that, in the present specification and the drawings, components having substantially the same functional configuration are denoted by the same reference signs, so that an overlapping description of these components is omitted.

Note that the description will be provided in the following order.

1. Background
   1.1. Surface Shape Calculation Method
   1.2. Problem of Calculation Method
2. First Embodiment
   2.1. Overview of First Embodiment
   2.2. Example of Configuration of System
   2.3. Example of Configuration of Microscope
   2.4. Example of Configuration of Information Processing Device
   2.5. Depth Calculation Processing
3. Second Embodiment
4. Third Embodiment
5. Fourth Embodiment
6. Fifth Embodiment
7. Sixth Embodiment
8. Seventh Embodiment
9. Eighth Embodiment
10. Ninth Embodiment
11. Tenth Embodiment
12. Other Embodiments
13. Adaptation Example
14. Supplementary Description 1. Background 1.1. Surface Shape Calculation Method First, before describing the details of embodiments of the present disclosure, a background that the present inventors have created the embodiments of the present disclosure will be described.

As a method of obtaining a 3D image in which a shape (unevenness) of an object is reproduced based on a captured image (RGB image) captured by an imaging device, for example, a method of directly calculating a surface shape (a depth to a surface) based on an RGB image by using machine learning such as a convolutional neural network (CNN) has been known. However, in a case where the depth is directly calculated by using the CNN based on the RGB image, there is uncertainty, and it is difficult to improve accuracy.

Figures 1, 2:
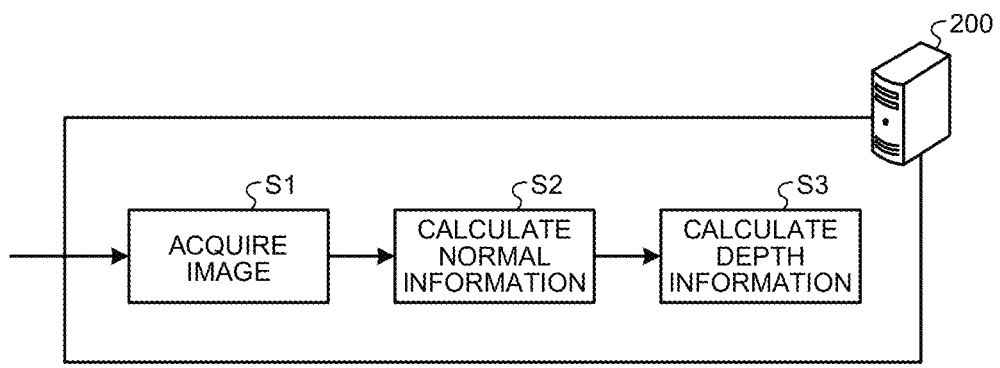
FIG. 1 is a diagram for describing a calculation method for calculating a depth based on a captured image.
FIG. 2 is a table for describing a rough shape of a surface of a target.

As another method of calculating the depth to the surface of the object based on the captured image, there is a method of calculating normal information of the surface of the object based on the captured image by using machine learning such as the CNN, and transforming the normal information into a depth by using an expression. Such a method will be described with reference to FIG. 1. FIG. 1 is a diagram for describing a calculation method for calculating a depth based on a captured image. The method described with reference to FIG. 1 is used by an information processing device 200, for example.

In such a method, the information processing device 200 first acquires a captured image captured by a microscope (Step S1). At this time, the information processing device 200 also acquires information regarding the microscope, for example. The information processing device 200 calculates a normal (normal information) of a surface of a target based on the captured image (Step S2). The information processing device 200 obtains the normal information as output data by inputting the captured image to a learning machine (model) trained using the CNN or the like, for example.

The information processing device 200 calculates a distance (depth information) to the surface of the target based on the normal information (Step S3). In a case where a distance between a sensor of the microscope and the target, which is one piece of information regarding the microscope, is known, the information processing device 200 can measure the distance to the surface of the target based on the normal information. Here, in a case where a user performs imaging of the target by using the microscope, a head-mounted portion of the microscope is brought into contact with the target to perform imaging. Therefore, the distance between the sensor of the microscope and the target is a known value corresponding to a length of the head-mounted portion.

Specifically, the information processing device 200 calculates a depth to the surface of the target based on the normal information by minimizing W in the following Expression (1).

[Math. 1]

$$W = \iint_\Omega [|Z_x - p|^2 + |Z_y - q|^2] dxdy + \lambda \iint_\Omega [|Z_x|^2 + |Z_y|^2] dxdy + \mu \iint_\Omega [|Z_{xx}|^2 + 2|Z_{xy}|^2 + |Z_{yy}|^2] dxdy \quad (1)$$

Note that parameters of Expression (1) are as follows.
p: an x direction of the calculated normal
q: a y direction of the calculated normal
$Z_x$: partial derivative of the depth to be obtained in the x direction (the x direction of the normal)
$Z_y$: partial derivative of the depth to be obtained in the y direction (the y direction of the normal)
$Z_{xx}$: second-order partial derivative of the depth to be obtained in the x direction (partial derivative in the x direction of the normal)
$Z_{yy}$: second-order partial derivative of the depth to be obtained in the y direction (partial derivative in the y direction of the normal)
$Z_{xy}$: second-order partial derivative of the depth to be obtained in the x direction and the y direction Note that x and y indicate coordinates on the captured image, and the x direction is, for example, a horizontal direction of the captured image, and the y direction is a vertical direction of the captured image.

When a Fourier transform (frequency transform) of Expression (1) is performed, Expression (2) is obtained. The depth to the surface of the target is calculated by minimizing this. Note that $Z_F$ in Expression (2) is obtained by the Fourier transform of the depth to be obtained, and u and v represent coordinates in a frequency space.

[Math. 2]

$$\frac{1}{2\pi} \int\int_\Omega [|juZ_F(u,v) - P(u,v)|^2 + |jvZ_F(u,v) - Q(u,v)|^2] dudv + \frac{\lambda}{2\pi} \int\int_\Omega [|juZ_F(u,v)|^2 + |jvZ_F(u,v)|^2] dudv + \frac{\mu}{2\pi} \int\int_\Omega [|-u^2 Z_F(u,v)|^2 + 2|-uvZ_F(u,v)|^2 + |-v^2 Z_F(u,v)|^2] dudv \to \text{minimum} \quad (2)$$

Expression (3) below is obtained by developing Expression (2), and the depth to the surface of the target is calculated by performing an inverse Fourier transform on Expression (3).

[Math. 3]

$$Z_F(u,v) = \frac{-juP(u,v) - jvQ(u,v)}{(1+\lambda)(u^2+v^2) + \mu(u^2+v^2)^2} \quad (3)$$

The information processing device 200 calculates the distance (depth) to the surface of the target by using the above-described transform of Expressions (1) to (3).

1.2. Problem of Calculation Method

In the above-described calculation method, the second and third rows on the right side of Expression (1) are cost terms in Expression (1), the second row represents the sum of absolute values of the normal, and the third row represents the sum of absolute values of the derivatives of the normal.

Here, in the above-described calculation method, the depth is calculated on the assumption that a weight ($\lambda,\mu$) of the cost term is small, that is, the sum of the absolute values of the normal is small, and the sum of the absolute values of the derivatives of the normal is small. The assumption that the sum of the absolute values of the normal is small (hereinafter, also referred to as Assumption 1) means that the surface of the target for which the depth is calculated is flat. The assumption that the sum of the absolute values of the derivatives of the normal is small (hereinafter, also referred to as Assumption 2) means that a curvature of the surface of the target for which the depth is calculated is small. That is, in the above-described calculation method, the depth to the target is calculated on the assumption that a rough surface shape of the target for which the depth is calculated is a flat surface shape.

Here, the rough shape of the surface of the target will be described with reference to FIG. 2. FIG. 2 is a table for describing the rough shape of the surface of the target. Note that, in FIG. 2, an actual shape of the surface of the target is indicated by a dotted line, and the rough shape of the surface of the target is indicated by a straight line. Further, the normal of the surface of the target is indicated by an arrow. In FIG. 2, the horizontal direction of the target is defined as the x direction, and the vertical direction is defined as a z direction (depth).

The rough shape of the surface of the target is the shape of the surface of the target in the entire captured image, and the rough shape being the flat surface shape means that there is little variation when the shape of the surface of the target in the entire captured image is viewed. Note that a change in local unevenness of the surface of the target is not included in the rough shape because it is a calculation target. The information processing device 200 can calculate the depth to the surface of the target with higher accuracy as the assumption of the cost term of the optimization formula shown in Expression (1) described above is satisfied, that is, the shape of the surface of the target in the entire captured image is closer to the flat surface shape.

For example, the target illustrated in (1) of the table of FIG. 2 has a shape in which a fine unevenness is included in a straight surface. Therefore, since the target illustrated in (1) satisfies both of Assumptions 1 and 2 described above (indicated by "◯" in the table), the information processing device 200 can calculate the depth of the target with high accuracy.

The target illustrated in (2) of the table of FIG. 2 has a shape in which a fine unevenness is included in a surface that is slightly curved upward. Therefore, the target illustrated in (2) slightly satisfies Assumption 1 described above (indicated by "Δ" in the table) and satisfies Assumption 2. Therefore, the information processing device 200 can calculate the depth of the target illustrated in (2) with high accuracy although the accuracy is lower than that of (1).

The target illustrated in (3) of the table of FIG. 2 has a shape in which a fine unevenness is included in a surface that is greatly curved upward on the left side. Therefore, the target illustrated in (3) does not satisfy both of Assumptions 1 and 2 (indicated by "x" in the table). Therefore, the information processing device 200 cannot accurately calculate the depth of the target illustrated in (3).

The target illustrated in (4) of the table of FIG. 2 has a stepped surface. As described above, since the target illustrated in (4) has a shape in which a fine unevenness is included in a surface having a plurality of straight surfaces having different heights and directions, the target illustrated in (4) does not satisfy both of Assumptions 1 and 2 described above. Therefore, the information processing device 200 cannot accurately calculate the depth of the target illustrated in (4).

As described above, in the above-described calculation method, there is a problem that the accuracy in calculating the depth is decreased in a case where the assumption that the rough shape of the surface of the depth calculation target is a flat shape is not satisfied.

Therefore, in view of such a situation, the present discloser has created each embodiment of the present disclosure related to the information processing device 200 capable of improving accuracy in shape measurement by improving the accuracy in depth calculation. Therefore, the details of each embodiment according to the present disclosure will be sequentially described below.

2. First Embodiment

2.1. Overview of First Embodiment

Figure 3:
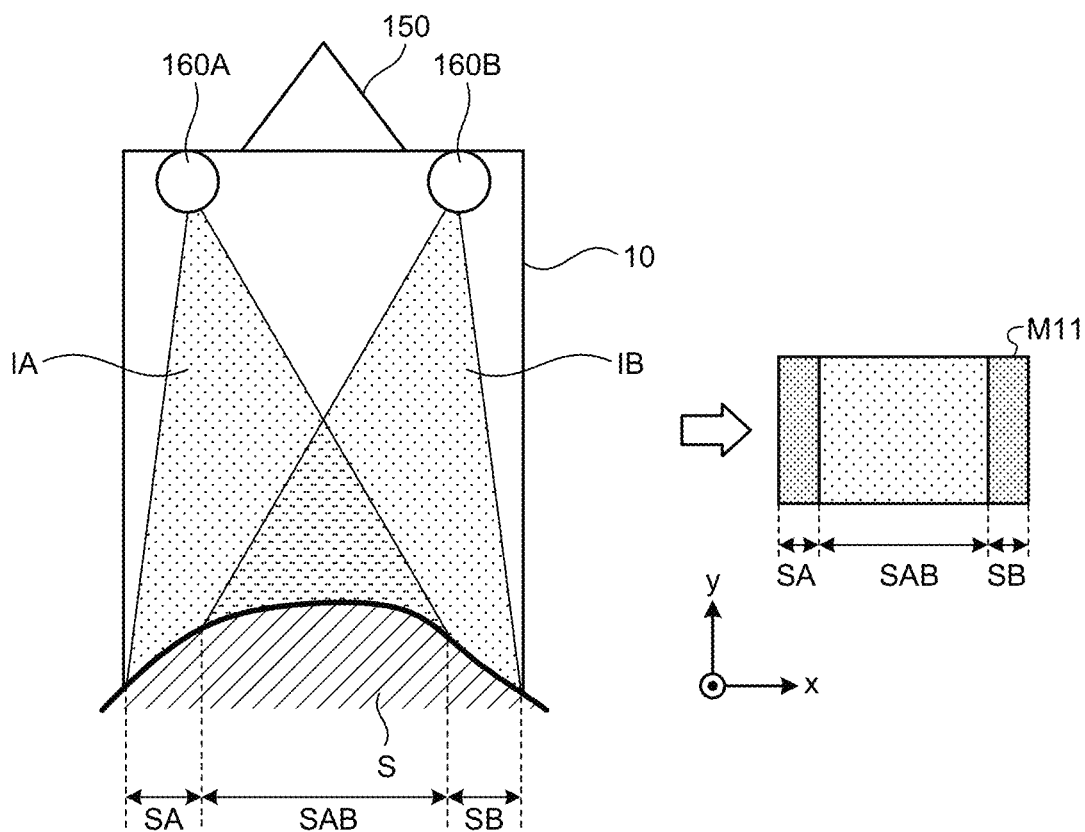
FIG. 3 is a diagram for describing an overview of a first embodiment of the present disclosure.

FIG. 3 is a diagram for describing an overview of a first embodiment of the present disclosure. An information processing device 200A (not illustrated) according to the first embodiment extracts a region (flat region) satisfying Assumptions 1 and 2 described above from a captured image, thereby suppressing deterioration of accuracy of shape information (depth information) regarding a shape of a surface of a target and improving accuracy in shape measurement.

First, the information processing device 200A acquires a captured image M11 obtained by imaging a target S by a sensor 150 of a microscope 100. The captured image M11 is an image obtained from reflected light of light IA and light IB emitted to the target S from a plurality of light sources 160A and 160B arranged at different positions, respectively.

Here, the microscope 100 will be briefly described. As illustrated in the left side of FIG. 3, the microscope 100 includes the sensor 150, a head-mounted portion 10 which is a cylindrical mechanism installed between the sensor 150 and an imaging target, and the plurality of light sources 160A and 160B. Note that the sensor 150 may be read as a lens, a camera, or the like. The microscope 100 is an imaging device that is used by a user holding the microscope in his/her hand and bringing the head-mounted portion 10 into contact with the target S to direct the sensor 150 toward the target S.

The microscope 100 exposes the target S with the reflected light of the light IA and the light IB simultaneously emitted from the light sources 160A and 160B to the target S to image the target S. At this time, for example, in a case where a rough shape of a surface of the target S is not a flat surface shape, occlusion (a region not irradiated with the light) occurs on the surface of the target S.

For example, the light IA emitted from the light source 160A hits a region SA and a region SAB in the surface of the target S, but does not hit a region SB. On the other hand, the light IB emitted from the light source 160B hits the region SB and the region SAB on the surface of the target S, but does not hit the region SA. The region SAB hit by both the light IA and the light IB from the plurality of light sources 160A and 160B is a flat region without occlusion.

As illustrated on the right side of FIG. 3, the captured image M11 of the microscope 100 is a dark image in which the regions SA and SB hit by only one of the light IA and the light IB of the light sources 160A and 160B have lower luminance values than that of the region SAB hit by both the light IA and the light IB.

Therefore, the information processing device 200A extracts the flat region SAB from the captured image M11 based on the luminance value of the captured image M11.

For example, the information processing device 200A extracts, as the flat region, the region SAB in which the luminance value of the captured image M11 is equal to or greater than a threshold.

The information processing device 200A calculates shape information (depth information) regarding the shape of the surface of the target S based on the information regarding the sensor 150 and the flat region SAB of the captured image M11. For example, the information processing device 200A acquires normal information of the flat region SAB by inputting the flat region SAB of the captured image M11 to the learning machine trained using the CNN. The information processing device 200A calculates the depth information regarding the depth to the surface of the target S by performing the transform on the acquired normal information by using the above-described Expressions (1) to (3).

In this manner, the information processing device 200A can improve the accuracy in shape measurement by extracting the region that satisfies the above-described Assumptions 1 and 2 of Expression (1) from the captured image M11.

Hereinafter, the details of an information processing system 1 including the information processing device 200A described above will be described.

2.2. Example of Configuration of System

Figure 4:
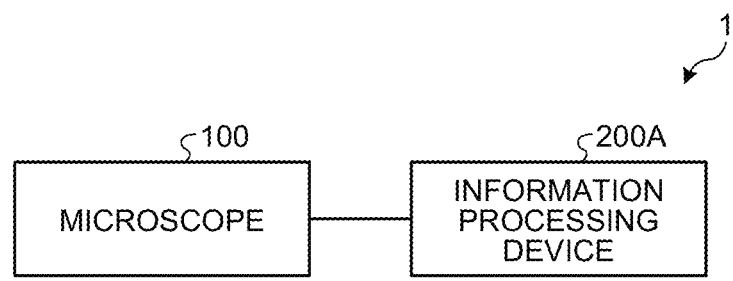
FIG. 4 is a block diagram illustrating an example of a configuration of an information processing system according to the first embodiment of the present disclosure.

FIG. 4 is a block diagram illustrating an example of a configuration of the information processing system 1 according to the first embodiment of the present disclosure. As illustrated in FIG. 4, the information processing system 1 includes the microscope 100 and the information processing device 200A.

The microscope 100 is an imaging device that is used by a user holding the microscope in his/her hand and directing the sensor 150 toward the imaging target S.

The information processing device 200A calculates the shape information regarding the shape of the surface of the imaging target S based on the captured image M11 captured by the microscope 100. The details of the information processing device 200A will be described later with reference to FIG. 6.

The microscope 100 and the information processing device 200A are connected by using, for example, a cable. Alternatively, the microscope 100 and the information processing device 200A may be directly connected by wireless communication such as Bluetooth (registered trademark) or near field communication (NFC). The microscope 100 and the information processing device 200A may be connected in a wired or wireless manner via, for example, a network (not illustrated). Alternatively, the microscope 100 and the information processing device 200A may transmit and receive a captured image via an externally mounted storage medium such as a hard disk, a magnetic disk, a magneto-optical disk, an optical disk, a USB memory, or a memory card. Furthermore, the microscope 100 and the information processing device 200A may be integrally configured. Specifically, for example, the information processing device 200A may be arranged inside a main body of the microscope 100.

2.3. Example of Configuration of Microscope

Figure 5:
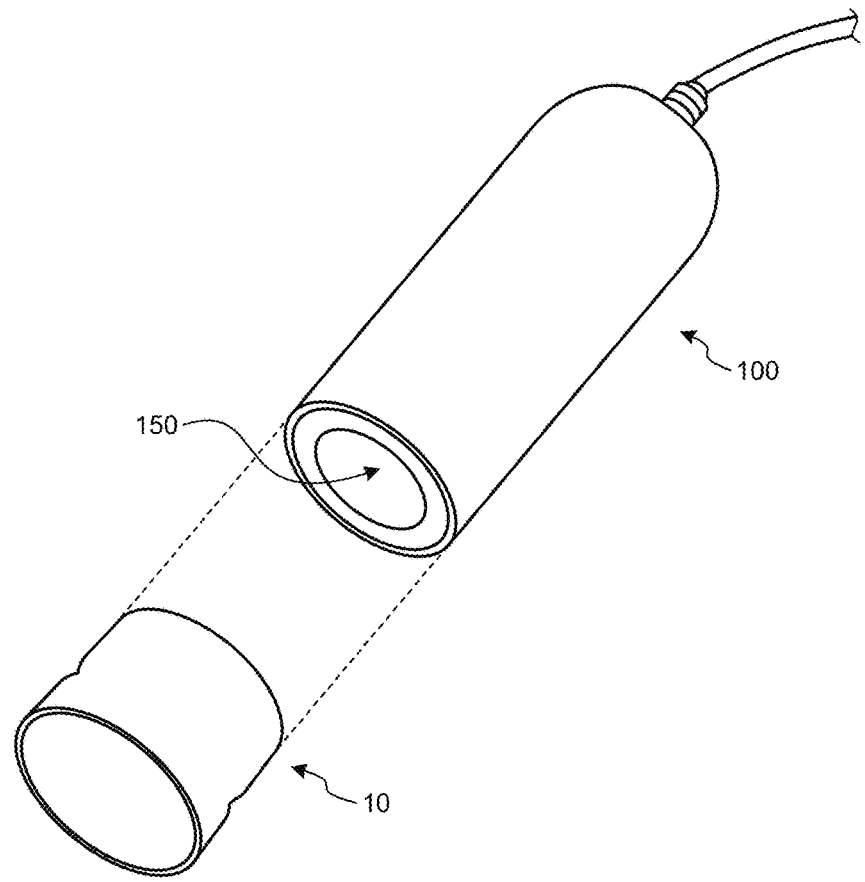
FIG. 5 is a diagram illustrating an example of a configuration of a microscope according to the first embodiment of the present disclosure.

FIG. 5 is a diagram illustrating an example of a configuration of the microscope 100 according to the first embodiment of the present disclosure. The microscope 100 includes the sensor 150 and the head-mounted portion 10 which is a cylindrical mechanism installed between the sensor 150 and the imaging target. In addition, the microscope 100 includes the point light sources 160A and 160B (not illustrated) arranged at different positions.

The head-mounted portion 10 is a mechanism mounted on a distal end of the microscope 100. The head-mounted portion 10 is also referred to as, for example, a tip head or a lens barrel. For example, a mirror may be provided inside the head-mounted portion 10, and the light emitted from the point light sources 160A and 160B may be totally reflected by a side surface of the head-mounted portion 10.

The user brings the head-mounted portion 10 into contact with the target S to image the target S. As a result, a distance between the sensor 150 and the target S is fixed, and it is possible to prevent a focus (focal length) from being shifted in imaging.

The microscope 100 includes the point light sources 160A and 160B provided inside the head-mounted portion 10. Therefore, the microscope 100 exposes the target S with the reflected light of the light IA and the light IB emitted from the point light sources 160A and 160B to the target S to image the target S. Note that the point light source in the present specification ideally means a light source based on a point, but there is practically no light source based on a point, and thus, the point light source includes a light source having an extremely small size (within several millimeters or less).

Note that a case where the point light source is used as an example of the light source will be described in the present specification, but the light source is not limited to the point light source. In addition, the number of light sources is not limited to two. A plurality of light sources may be provided, and three or more light sources may be provided as long as the light sources are arranged at different positions, respectively.

2.4. Example of Configuration of Information Processing Device

Figure 6:
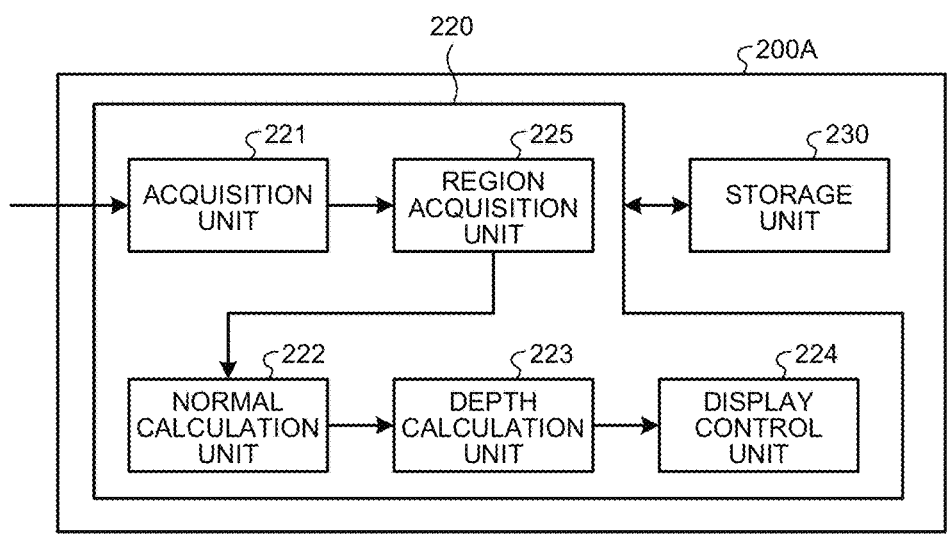
FIG. 6 is a block diagram illustrating an example of a configuration of an information processing device according to the first embodiment of the present disclosure.

FIG. 6 is a block diagram illustrating an example of a configuration of the information processing device 200A according to the first embodiment of the present disclosure. The information processing device 200A includes a control unit 220 and a storage unit 230.

(Control Unit)

The control unit 220 controls an operation of the information processing device 200A. The control unit 220 includes an acquisition unit 221, a region acquisition unit 225, a normal calculation unit 222, a depth calculation unit 223, and a display control unit 224. The respective functional units including the acquisition unit 221, the region acquisition unit 225, the normal calculation unit 222, the depth calculation unit 223, and the display control unit 224 are implemented by, for example, the control unit 220 executing a program stored inside the control unit 220 by using a random access memory (RAM) or the like as a work area. Note that an internal structure of the control unit 220 is not limited to the configuration illustrated in FIG. 6, and the control unit 220 may have another configuration as long as information processing as described later is performed. Furthermore, a connection relationship between the respective processing units included in the control unit 220 is not limited to a connection relationship illustrated in FIG. 6, and may be another connection relationship.

(Acquisition Unit)

The acquisition unit 221 acquires the captured image M11 captured by the microscope 100 and information regarding the microscope 100. The information regarding the microscope 100 includes information regarding a structure of the microscope 100, such as a focal length f and a length d of the head-mounted portion 10, for example.

For example, the acquisition unit 221 may control the point light sources 160A and 160B and the sensor 150 of the microscope 100. In this case, the acquisition unit 221 controls the point light sources 160A and 160B so that the light IA and the light IB are simultaneously emitted from the point light sources 160A and 160B. In addition, the acquisition unit 221 controls the sensor 150 so that the sensor 150 images the target S while the light IA and the light IB are simultaneously emitted from the point light sources 160A and 160B. In this manner, the information processing device 200A may control the microscope 100.

Alternatively, the acquisition unit 221 may acquire information regarding an imaging condition in addition to the captured image M11. The information regarding the imaging condition is, for example, information indicating that the captured image M11 is an image captured while the light IA and the light IB are simultaneously emitted from the point light sources 160A and 160B. In this case, the region acquisition unit 225 to be described later extracts the flat region SAB from the captured image M11 according to, for example, the imaging condition.

(Region Acquisition Unit)

Figure 7:
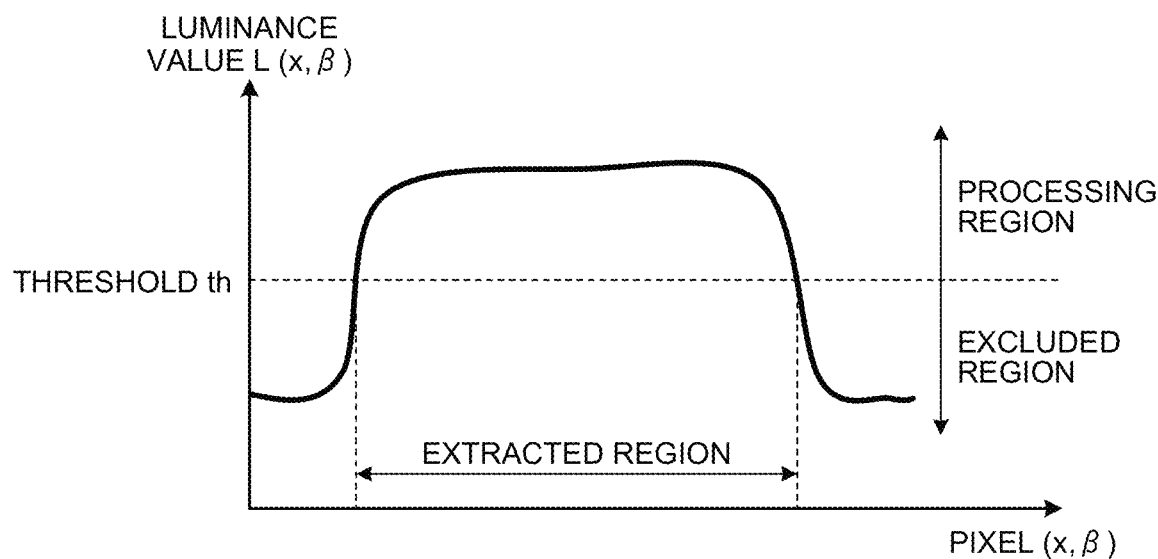
FIG. 7 is a diagram illustrating an example of a luminance value of the captured image.

The region acquisition unit 225 extracts the flat region SAB from the captured image M11. For example, the region acquisition unit 225 compares a luminance value $L(x,y)$ of each pixel of the captured image M11 with a threshold th. As illustrated in FIG. 7, the region acquisition unit 225 sets a region including a pixel whose luminance value $L(x,y)$ is equal to or more than the threshold th as a processing region, and sets a region including a pixel whose luminance value $L(x,y)$ is less than the threshold th as an excluded region. Note that FIG. 7 is a diagram illustrating an example of the luminance value of the captured image M11, and FIG. 7 illustrates a relationship between a luminance value $L(x,\beta)$ and a pixel $(x,\beta)$, in which a value of a y axis is a predetermined value "$\beta$".

Note that, in a case where the captured image M11 is an RGB image, the luminance value $L(x,y)$ is calculated by using an expression $L(x,y)=(R(x,y)+2G(x,y)+B(x,y))/4$. $R(x,y)$ is a red (R) component of a pixel value of a pixel $(x,y)$, $G(x,y)$ is a green (G) component of the pixel value of the pixel $(x,y)$, and $B(x,y)$ is a blue (B) component of the pixel value of the pixel $(x,y)$.

The region acquisition unit 225 compares the luminance value $L(x,y)$ with the threshold th for all the pixels to acquire, as an extracted region (flat region SAB) to be extracted from the captured image M11, the region determined as the processing region.

Figure 8:
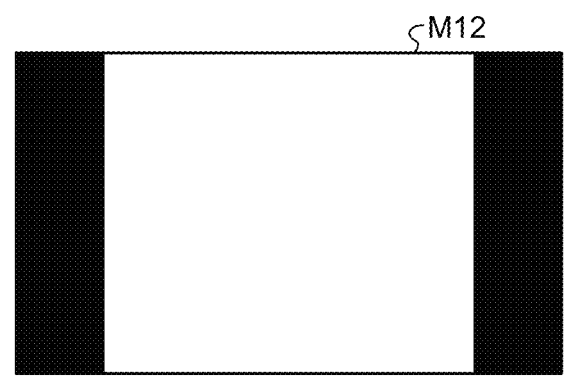
FIG. 8 is a diagram illustrating an example of a mask image generated by a region acquisition unit.

For example, the region acquisition unit 225 generates a mask image M12 illustrated in FIG. 8 by setting the pixel to white in a case where the luminance value $L(x,y)$ of the pixel is equal to or more than the threshold th and setting the pixel to black in a case where the luminance value $L(x,y)$ is less than the threshold th. Note that FIG. 8 is a diagram illustrating an example of the mask image M12 generated by the region acquisition unit 225.

Figure 9:
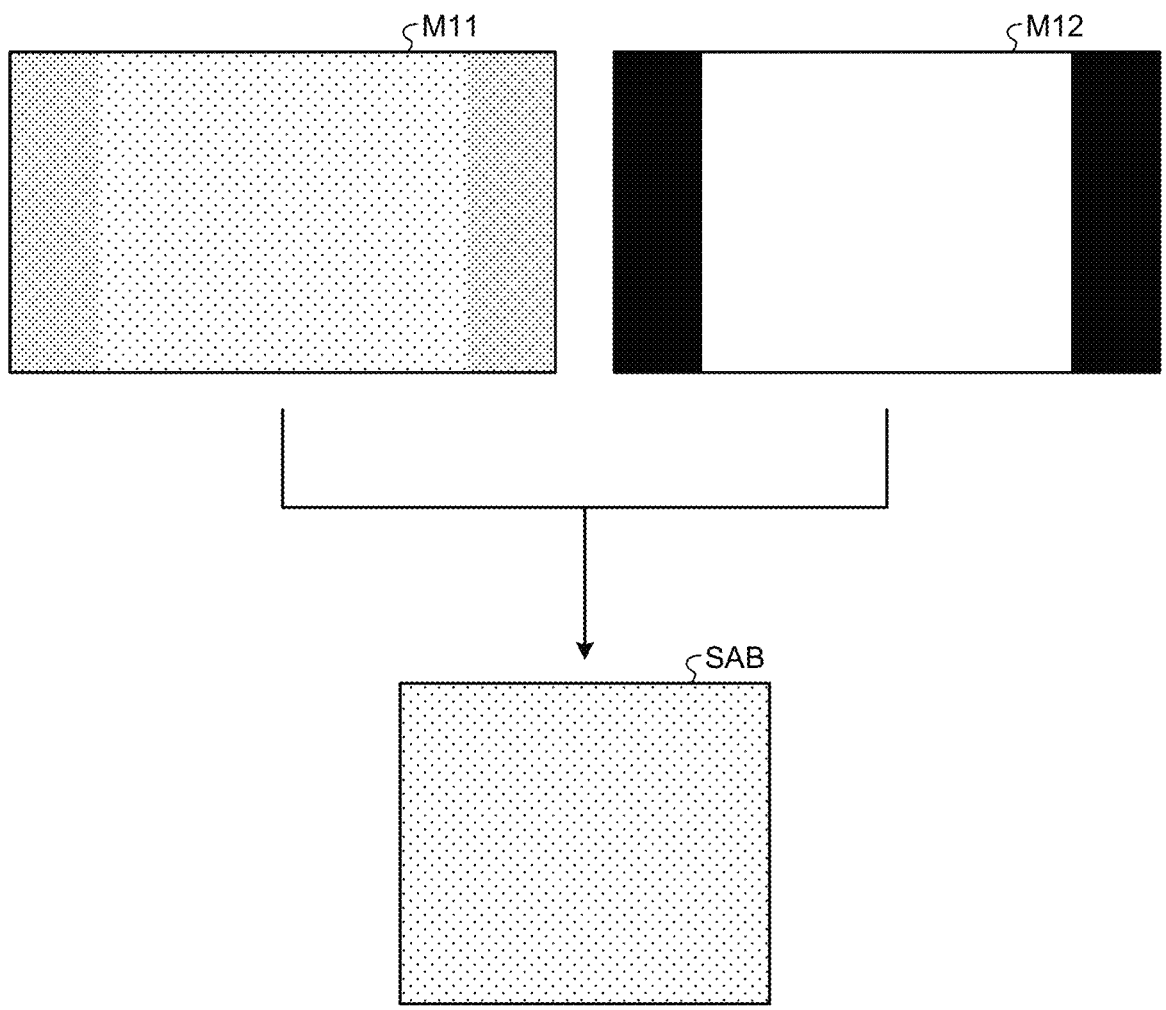
FIG. 9 is a diagram for describing an example of acquisition of a flat region by the region acquisition unit.

As illustrated in FIG. 9, the region acquisition unit 225 compares the generated mask image M12 with the captured image M11, and extracts pixels in which the mask image M12 is white in the same coordinates from the captured image M11, thereby acquiring the flat region SAB. Note that FIG. 9 is a diagram for describing an example of acquisition of the flat region SAB by the region acquisition unit 225.

Alternatively, the region acquisition unit 255 may generate the mask image M12 by setting the luminance value of the pixel to "1" in a case where the luminance value L(x,y) of the pixel is equal to or more than the threshold th and setting the luminance value of the pixel to "0" in a case where the luminance value L is less than the threshold th. In this case, the region acquisition unit 255 acquires the flat region SAB by multiplying the captured image M11 and the mask image M12.

The region acquisition unit 255 outputs the acquired flat region SAB to the normal calculation unit 222. Note that the mask image M12 generated by the region acquisition unit 255 may be output to the normal calculation unit 222, and the normal calculation unit 222 may acquire the flat region SAB from the captured image M11 by using the mask image M12.

(Normal Calculation Unit)

The normal calculation unit 222 calculates the normal information for the surface of the target S as a normal image based on the flat region SAB of the captured image M11. The normal calculation unit 222 generates the normal image by using the CNN, for example. The normal calculation unit 222 generates the normal image by using the learning machine trained in advance using the CNN. The number of input channels of a learning machine 300 (see FIG. 11) is three corresponding to RGB of an input image (here, the flat region SAB) or is one corresponding to a grayscale of the input image. Furthermore, the number of output channels of the learning machine 300 is three corresponding to RGB of an output image (here, the normal image). Resolution of the output image is assumed to be equal to resolution of the input image.

Figure 10:
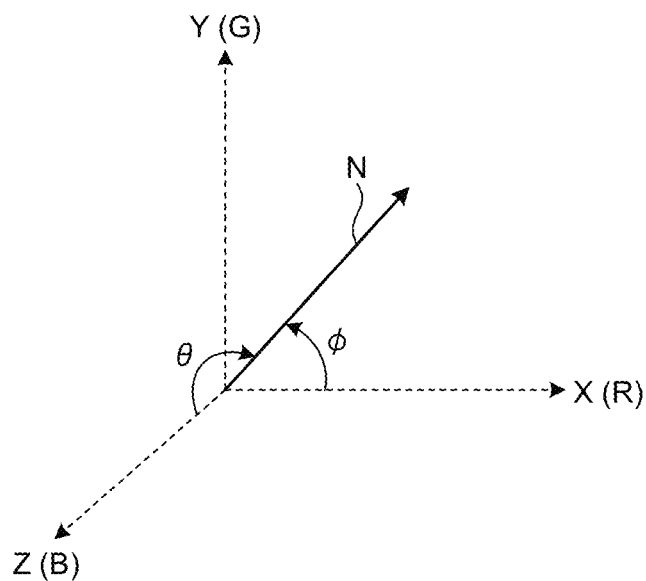
FIG. 10 is a diagram for describing an example of normal information.

Here, a relationship between the normal information and RGB of the normal image will be described with reference to FIG. 10. FIG. 10 is a diagram for describing an example of the normal information. It is assumed that a normal N illustrated in FIG. 10 is a normal vector in a predetermined pixel of the captured image M11 obtained by imaging the target S. In this case, a relationship of the following Expression (4) is established between a normal N (θ,ϕ) in a polar coordinate system and a normal N (x,y,z) in an orthogonal coordinate system, in which a zenith angle of the normal N is θ and an azimuth angle is ϕ. Note that the normal N is assumed to be a unit vector.

[Math.4]

$$x = \cos \phi \sin \theta$$

$$y = \sin \phi \sin \theta$$

$$z = \cos \theta \quad (4)$$

The normal information is the normal N (x,y,z) in the above-described orthogonal coordinate system, and is calculated for each pixel of the flat region SAB of the captured image M11, for example. Furthermore, the normal image is an image obtained by replacing the normal information of each pixel with RGB. That is, the normal image is an image obtained by replacing x of the normal N with R (red), replacing y with G (green), and replacing z with B (blue).

The description returns to FIG. 6. The normal calculation unit 222 generates the normal image, which is the output image, by inputting the flat region SAB as the input image to the learning machine 300. It is assumed that the learning machine 300 is generated in advance by learning the weight in the CNN using a ground truth of learning as a normal.

Figure 11:
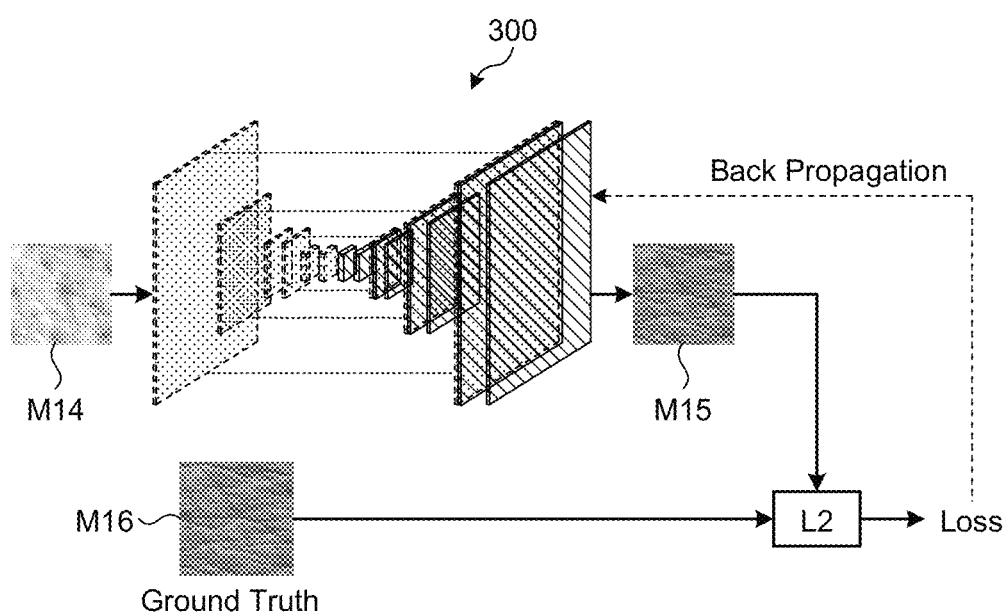
FIG. 11 is a diagram for describing a learning machine according to an embodiment of the present disclosure.

Here, a method of generating the learning machine 300 will be described with reference to FIG. 11. FIG. 11 is a diagram for describing the learning machine 300 according to an embodiment of the present disclosure. Here, in order to simplify the description, it is assumed that the control unit 220 of the information processing device 200A generates the learning machine 300, but the learning machine 300 may be generated by, for example, another information processing device (not illustrated) or the like.

In the example illustrated in FIG. 11, the information processing device 200A calculates similarity between an output image M15 in a case where an input image M14 is input to the learning machine 300 and a normal image M16 which is the ground truth of learning. Here, the information processing device 200A calculates a least square error (L2) between the output image M15 and the normal image M16, and performs learning processing with L2 as a loss. The information processing device 200A updates the weight of the learning machine 300, for example, by back-propagating the calculated loss. As a result, the information processing device 200A generates the learning machine 300 that outputs the normal image when the captured image is input.

Note that, here, the learning machine 300 is generated using the CNN as an example of machine learning, but the present invention is not limited thereto. As the machine learning, the learning machine 300 may be generated using various methods such as a recurrent neural network (RNN) in addition to the CNN. Furthermore, in the above-described example, the weight of the learning machine 300 is updated by back-propagating the calculated loss, but the present invention is not limited thereto. In addition to the back-propagation, the weight of the learning machine 300 may be updated using an arbitrary learning method such as stochastic gradient descent. In the above-described example, the loss is the least square error, but is not limited thereto. The loss may be a minimum average error.

The description returns to FIG. 6. The normal calculation unit 222 generates the normal image by using the generated learning machine 300. The normal calculation unit 222 outputs the calculated normal image to the depth calculation unit 223.

(Depth Calculation Unit)

The depth calculation unit 223 calculates the distance (depth) from the sensor 150 to the target S by performing the transform using the above-described Expressions (1) to (3) with each pixel value of the normal image as an input. Specifically, the depth calculation unit 223 calculates Z' by performing inverse Fourier transform on the above-described Expression (3) as follows, and calculates a depth Z to be obtained as Z=Z'×P.

[Math. 5]

$$Z_F(u, v) = \frac{-juP(u, v) - jvQ(u, v)}{(1 + \lambda)(u^2 + v^2) + \mu(u^2 + v^2)^2} \quad (3)$$

↓ Inverse Fourier transform $$Z'$$

↓ $Z = Z' \times P$ $$Z$$

Note that parameters of the above-described Expression (3) and the like are as follows.

P(u,v): Fourier transform of the normal in the x direction
Q(u,v): Fourier transform of the normal in the y direction
u,v: coordinates of each pixel in the frequency space
P: a length [μm] per pixel (one pixel) of the captured image xy
$Z_F$: Fourier transform of the depth to be obtained
Z': the depth [pixel] per pixel to be obtained
Z: the depth [μm] to be obtained P (the length [μm] per pixel (one pixel) of the captured image xy) is a parameter whose value is determined based on the configuration of the sensor 150 of the imaging device (microscope 100).

Figure 12:
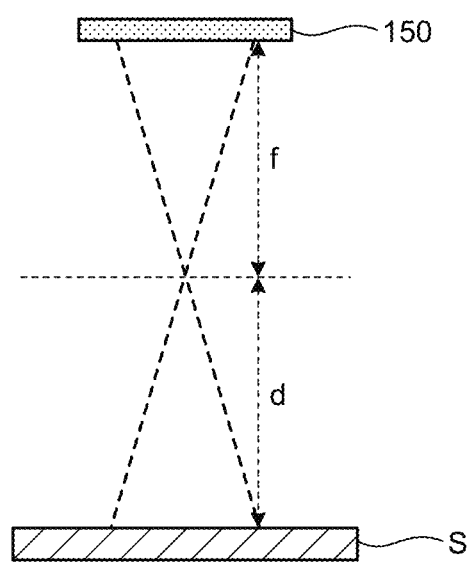
FIG. 12 is a diagram for describing a length per pixel of the captured image.

For example, as illustrated in FIG. 12, it is assumed that the focal length of the sensor 150 is f [mm] and a length of a housing (head-mounted portion 10) is d [mm]. Furthermore, the actual length P per pixel of the captured image is P=(d×p)/f [μm] based on P:d=p:f, in which a pixel pitch of the sensor 150 is p [μm]. Note that FIG. 12 is a diagram for describing the length per pixel of the captured image.

The depth calculation unit 223 calculates the depth of the target S for each pixel of the captured image M11, for example, based on the normal image and the information regarding the sensor 150. The information regarding the sensor 150 is, for example, information regarding a structure of the sensor 150, and specifically, information regarding the focal length of the sensor 150 and the distance between the sensor 150 and the target S described above. In a case where the imaging device is the microscope 100, the distance between the sensor 150 and the target S is the length d of the head-mounted portion 10.

(Display Control Unit)

Figure 13:
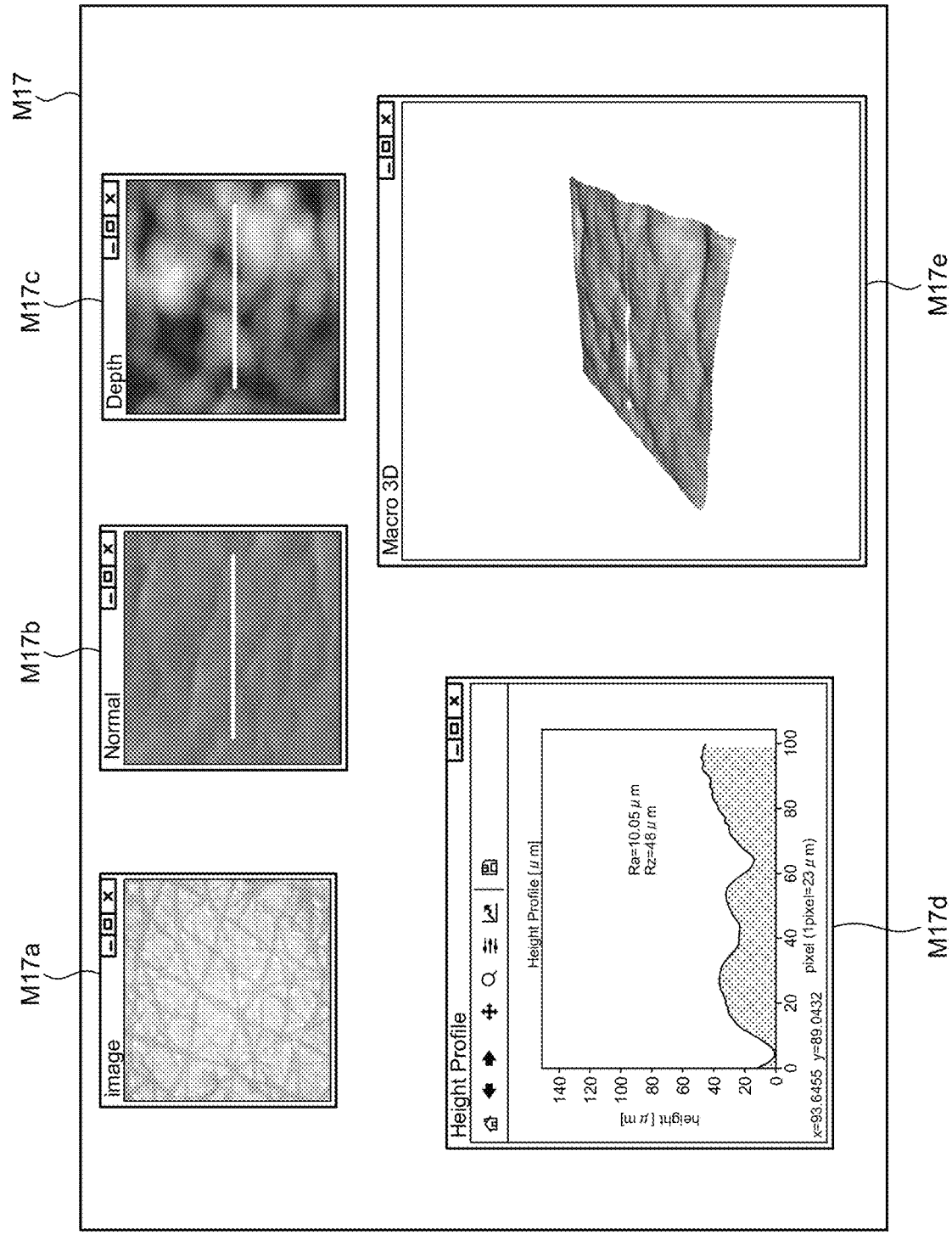
FIG. 13 is a diagram illustrating an example of an image displayed on a display unit by a display control unit.

The display control unit 224 displays various images on a display unit (not illustrated) such as a liquid crystal display. FIG. 13 is a diagram illustrating an example of an image M17 displayed on the display unit by the display control unit 224. As illustrated in FIG. 13, the display control unit 224 causes the display unit to display, for example, the image M17 including a captured image M17a, a normal image M17b, a depth image M17c, an image M17d showing a depth graph, and a 3D image M17e of the target S.

The captured image M17a is, for example, an image obtained by cutting the flat region SAB from the captured image M11 captured by the microscope 100. The normal image M17b is an image in which the normal information of the captured image M17a is displayed in RGB. The depth image M17c is an image indicating the depth in each pixel of the captured image M17a, and shows that, for example, the lighter the color is, the larger the depth is (the larger the distance from the sensor 150 to the target S is). The image M17d showing the depth graph is an image in which a graph of the depth on a straight line shown in the normal image M17b, the depth image M17c, and the 3D image M17e of the target S is displayed. The 3D image M17e of the target S is an image in which the target S is three-dimensionally displayed based on the depth image M17c.

In this manner, the display control unit 224 may display the depth graph or the three-dimensional image on the display unit in addition to the captured image, the generated normal image, and the depth image.

(Storage Unit)

The storage unit 230 is implemented by a read only memory (ROM) that stores a program to be used for processing performed by the control unit 220, an operation parameter, or the like, and a random access memory (RAM) that temporarily stores parameters that appropriately change.

2.5. Depth Calculation Processing

Figure 14:
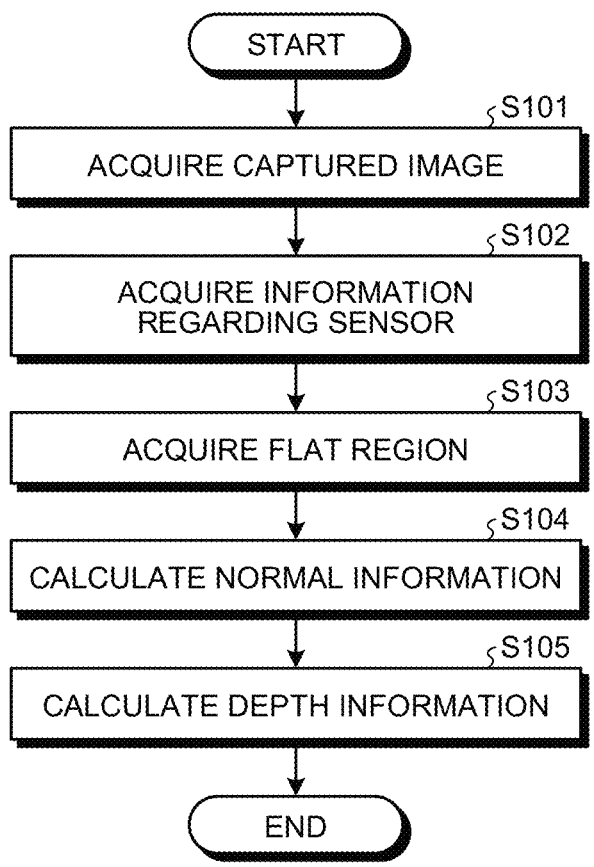
FIG. 14 is a flowchart for describing an example of depth calculation processing according to the first embodiment of the present disclosure.

FIG. 14 is a flowchart for describing an example of depth calculation processing according to the first embodiment of the present disclosure. The depth calculation processing illustrated in FIG. 14 is implemented by the control unit 220 of the information processing device 200A executing a program. The depth calculation processing illustrated in FIG. 14 is performed after the microscope 100 captures the captured image M11. Alternatively, the depth calculation processing illustrated in FIG. 14 may be performed in response to an instruction from the user.

As illustrated in FIG. 14, the control unit 220 acquires the captured image M11 from the microscope 100, for example (Step S101). Alternatively, the control unit 220 may acquire the captured image M11 from another device via, for example, a network (not illustrated). Examples of another device include another information processing device and a cloud server.

The control unit 220 acquires the information regarding the sensor 150 (Step S102). The control unit 220 may acquire the information regarding the sensor 150 from the microscope 100. Alternatively, in a case where the sensor information regarding the sensor 150 is stored in the storage unit 230, the control unit 220 may acquire the sensor information from the storage unit 230. Furthermore, the control unit 220 may acquire the sensor information by, for example, an input from the user.

The control unit 220 acquires the flat region SAB from the acquired captured image M11 (Step S103). Specifically, the control unit 220 extracts, as the flat region SAB, the region in which the luminance value of each pixel of the captured image M11 is equal to or more than the threshold th.

The control unit 220 calculates the normal information of the acquired flat region SAB (Step S104). Specifically, the control unit 220 inputs the flat region SAB as the input image to the learning machine 300 to generate, as the output image, the normal image including the normal information.

The control unit 220 calculates the depth information based on the normal information and the information regarding the sensor 150 (Step S105). Specifically, the control unit 220 calculates the depth information by performing, on the normal information, the transform based on the above-described Expression (3) or the like.

As described above, the information processing device 200A according to the first embodiment includes the control unit 220. The control unit 220 acquires the captured image M11 obtained by the sensor 150 capturing the target S. The captured image M11 is an image obtained from the reflected light of the light IA and the light IB emitted to the target S from the plurality of point light sources 160A and 160B arranged at different positions, respectively. The control unit 220 extracts the flat region SAB from the captured image M11 based on the luminance value of the captured image M11. The control unit 220 calculates the shape information (depth information) regarding the shape of the surface of the target S based on the information regarding the sensor 150 and the flat region SAB of the captured image M11.

In particular, the information processing device 200A according to the first embodiment acquires the flat region SAB from the captured image M11 obtained from the reflected light of the light IA and the light IB simultaneously emitted from the plurality of point light sources 160A and 160B to the target S.

As described above, as the information processing device 200A acquires the flat region SAB, it is possible to satisfy Assumptions 1 and 2 in the transform performed by the depth calculation unit 223, and it is possible to suppress a decrease in depth calculation accuracy. As a result, the information processing device 200A can improve the accuracy in shape measurement.

3. Second Embodiment

In the first embodiment, a case where the information processing device 200A calculates the depth based on the captured image M11 captured by the microscope 100 while the plurality of point light sources 160A and 160B simultaneously emit the light IA and the light IB has been described. In addition to the above example, the information processing device 200A may calculate the depth based on a captured image captured by the microscope 100 while light is emitted from one point light source. Therefore, in a second embodiment, an example in which an information processing device 200A calculates the depth based on a captured image that is obtained from reflected light of light emitted from one of a plurality of point light sources 160A and 160B to the target S and is obtained for each of the point light sources 160A and 160B will be described. Note that the information processing device 200A according to the second embodiment has the same configuration and is operated in the same manner as the information processing device 200A according to the first embodiment except for operations of an acquisition unit 221 and a region acquisition unit 225, and thus, is denoted by the same reference sign, and a part of description thereof will be omitted.

Figure 15:
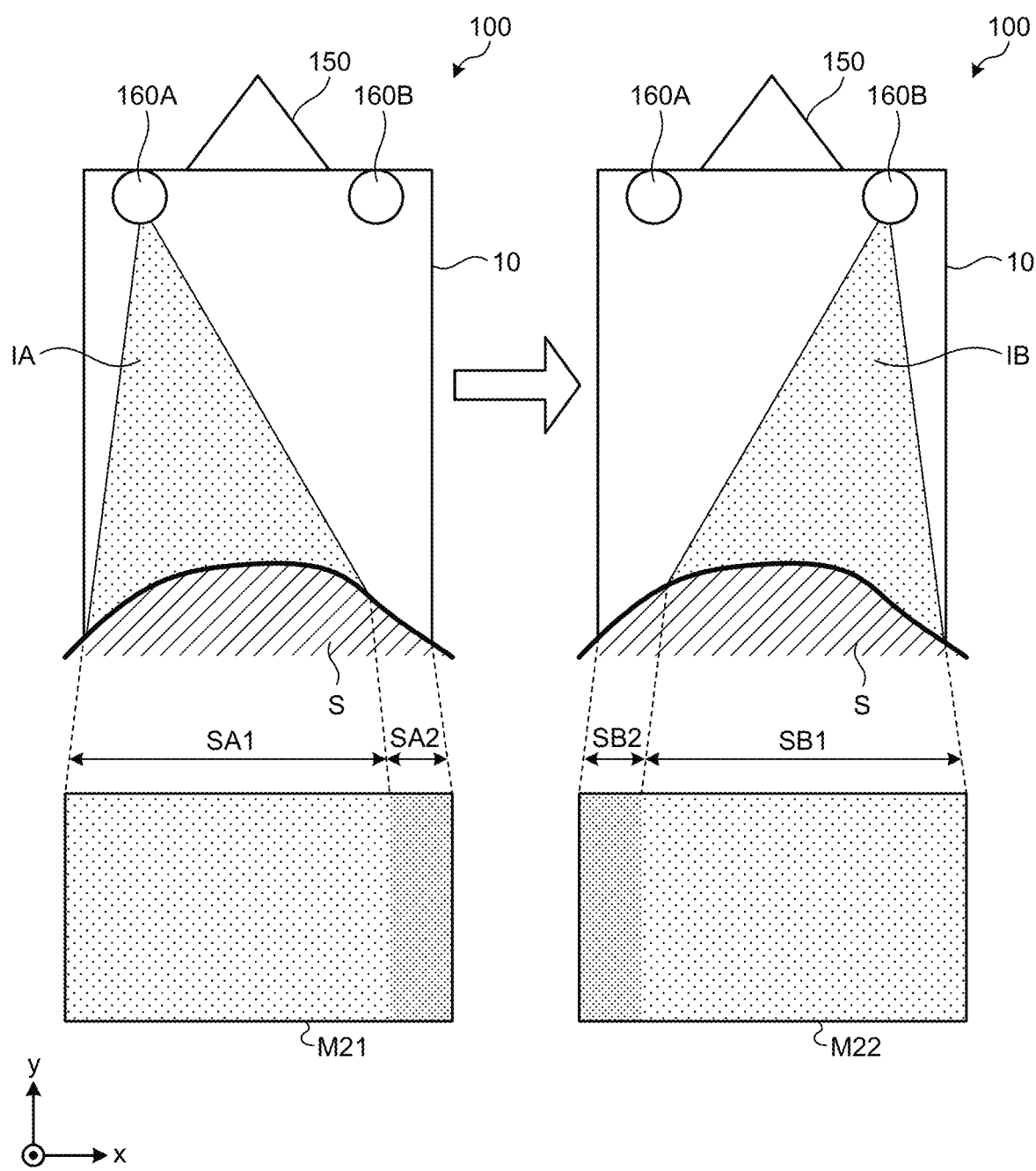
FIG. 15 is a diagram for describing captured images acquired by an acquisition unit according to a second embodiment of the present disclosure.

FIG. 15 is a diagram for describing captured images M21 and M22 acquired by the acquisition unit 221 according to the second embodiment of the present disclosure.

As illustrated in FIG. 15, a microscope 100 first emits light IA from the point light source 160A to image the target S. At this time, for example, in a case where a rough shape of a surface of the target S is not a flat surface shape, occlusion (a region not irradiated with the light) occurs on the surface of the target S.

For example, the light IA emitted from the light source 160A hits a region SA1 in the surface of the target S, but does not hit a region SA2. In this case, for example, as illustrated in FIG. 15, the acquisition unit 221 acquires the captured image M21 in which the region SA2 is darker than the region SA1.

Subsequently, the microscope 100 emits light IB from the point light source 160B to image the target S. At this time, similarly to the case where the light IA is emitted from the point light source 160A, occlusion (a region not irradiated with the light) occurs on the surface of the target S.

For example, the light IB emitted from the light source 160B hits a region SB1 on the surface of the target S, but does not hit a region SB2. In this case, for example, as illustrated in FIG. 15, the acquisition unit 221 acquires the captured image M22 in which the region SB2 is darker than the region SB1.

In this manner, the acquisition unit 221 acquires the captured images M21 and M22 captured by the microscope 100 sequentially turning on the two point light sources 160A and 160B.

The region acquisition unit 225 acquires the flat region SAB from the captured images M21 and M22 acquired by the acquisition unit 221. As described above, the light IA and the light IB of both the point light sources 160A and 160B hit the flat region SAB. In other words, an occlusion region that is not hit by at least one of the light IA or the light IB is a non-flat region. As described above, in the captured images M21 and M22, the light IA and the light IB from the point light sources 160A and 160B hit the flat region SAB, such that the luminance values of the pixels in the flat region SAB in both the captured images M21 and M22 are substantially the same.

Therefore, the region acquisition unit 225 acquires the flat region SAB based on the luminance values of the captured images M21 and M22. The region acquisition unit 225 extracts, as the flat region SAB, a region in which the luminance value is not changed or the change of the luminance value is small (smaller than a threshold th2) in the pixel corresponding to each of the captured images M21 and M22.

Figure 16:
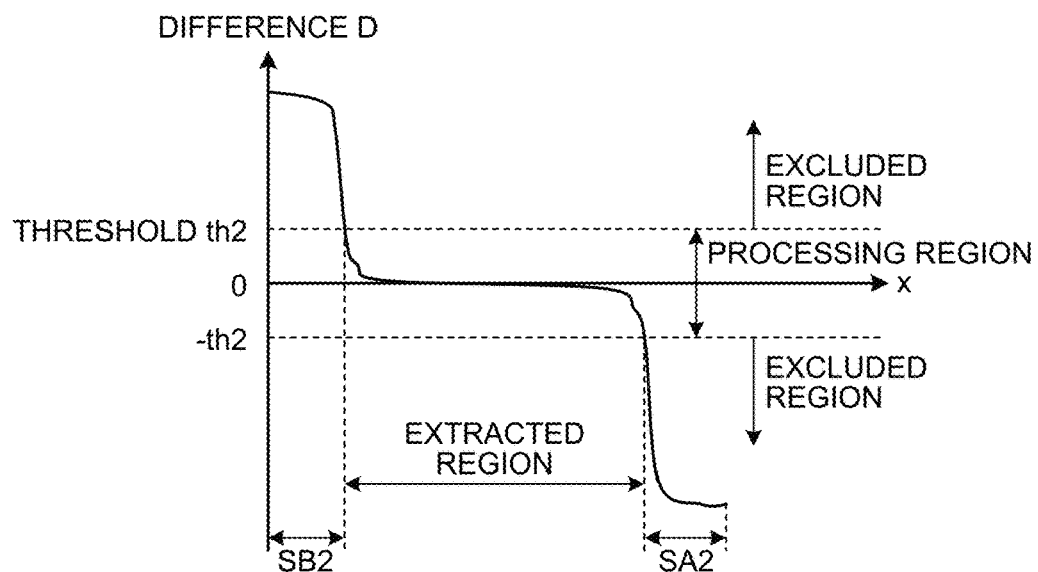
FIG. 16 is a diagram for describing the captured image acquired by the acquisition unit according to the second embodiment of the present disclosure.

A specific method of acquiring the flat region SAB by the region acquisition unit 225 will be described with reference to FIG. 16. FIG. 16 is a diagram for describing acquisition of the flat region by the region acquisition unit 225 according to the second embodiment of the present disclosure.

The region acquisition unit 225 calculates, for example, a difference $D(x,y)=L1(x,y)-L2(x,y)$ in luminance value of a corresponding pixel $(x,y)$ between the captured images M21 and M22. Note that $L1(x,y)$ is the luminance value of the pixel $(x,y)$ of the captured image M21, and $L2(x,y)$ is the luminance value of the pixel $(x,y)$ of the captured image M22. FIG. 16 is a graph illustrating a relationship between the difference D and x in a case where y of the pixel is fixed to a predetermined value. Note that, as illustrated in FIG. 15, a horizontal direction of the captured images M21 and M22 is the x direction, and a vertical direction thereof is the y direction.

For example, in the region SB2 illustrated in FIG. 16, the luminance value of the captured image M21 is high, and the luminance value of the captured image M22 is low (see FIG. 15). Therefore, the value of the difference D in the region SB2 becomes large in a positive direction. On the other hand, in the region SA2 illustrated in FIG. 16, the luminance value of the captured image M21 is low, and the luminance value of the captured image M22 is high (see FIG. 15). Therefore, the value of the difference D in the region SA2 becomes large in a negative direction. In addition, in the regions other than the regions SB2 and SA2, since both of the captured images M21 and M22 have substantially the same high luminance values, the difference D becomes close to 0.

Therefore, the region acquisition unit 225 sets the region SB2 where the difference D is equal to or larger than the threshold th2 as the excluded region for which the depth calculation is not performed. Further, the region acquisition unit 225 sets the region SA2 where the difference D is equal to or smaller than the threshold $-th2$ as the excluded region for which the depth calculation is not performed. The region acquisition unit 225 sets a region where the difference D is within a range of the threshold $\pm th2$ as the processing region for which the depth calculation is to be performed. The region acquisition unit 225 acquires the region determined as the processing region as the extracted region (flat region SAB) to be extracted from the captured images M21 and M22.

More specifically, the region acquisition unit 225 performs threshold determination on an absolute value $abs(D)$ of the difference D described above, sets, as a black region, a region including a pixel in which the absolute value $abs(D)$ of the difference D is equal to or larger than the threshold th2, and sets, as a white region, a region including a pixel in which the absolute value $abs(D)$ of the difference D is smaller than the threshold th2, thereby generating the mask image M12 illustrated in FIG. 8, for example. For example, the region acquisition unit 225 compares the generated mask image M12 with the captured image M21, and extracts pixels in which the mask image M12 is white in the same coordinates from the captured image M21, thereby acquiring the flat region SAB. Alternatively, the region acquisition unit 225 may compare the mask image M12 with the captured image M22 to acquire the flat region SAB. Note that processing after generating the mask image M12 is the same as that in the first embodiment.

In the second embodiment, one of the point light sources 160A and 160B emits light to perform imaging. In this case, as compared with a case of simultaneous light emission as in the first embodiment described above, the amount of light hitting the target S can be suppressed to be low, such that an overall brightness of the captured images M21 and M22 can be suppressed and a contrast can be maintained to be high. Therefore, it is possible to increase the difference between the luminance value of the region hit by the light and the luminance value of the occlusion region that is not hit by the light in the captured images M21 and M22. As a result, the region acquisition unit 225 can more easily acquire the flat region SAB from the captured images M21 and M22.

Meanwhile, in the information processing device 200A according to the first embodiment, since the number of captured images M11 to be acquired is only one, an image acquisition time can be reduced to half the time of the second embodiment. Furthermore, when the target S or a sensor 150 moves while the captured images M21 and M22 are sequentially captured, the region acquisition unit 225 needs to perform processing such as alignment of the captured images M21 and M22, for example, before acquiring the flat region SAB. Therefore, in a case where the depth calculation is performed in real time, it is desirable to perform the depth calculation using the information processing device 200A according to the first embodiment that has a short image acquisition time and does not require the processing such as alignment.

As described above, the information processing device 200A according to the second embodiment acquires the captured images M21 and M22 obtained from the reflected light of the light IA and the light IB emitted from one of the plurality of point light sources 160A and 160B to the target S for each of the point light sources 160A and 160B. The information processing device 200A extracts, as the flat region SAB, a region in which a change in luminance value (the absolute value of the difference D) between the plurality of captured images M21 and M22 acquired for each of the point light sources 160A and 160B is smaller than the predetermined threshold th2.

As a result, the information processing device 200A can increase the contrast of the captured images M21 and M22, improve accuracy in extracting the flat region SAB, and improve the accuracy in shape measurement.

Note that, here, a case where the microscope 100 includes two point light sources 160A and 160B has been described as an example, but the number of point light sources is not limited to two. For example, the microscope 100 may include three or more point light sources.

In this case, the microscope 100 sequentially turns on three or more point light sources to image the target S. The information processing device 200A acquires a plurality of captured images captured by the microscope 100. The information processing device 200A acquires, as the flat region SAB, a region in which a change in luminance value is small among the plurality of acquired captured images, in other words, a region in which an absolute value of a difference in luminance value of a corresponding pixel between the plurality of captured images is smaller than the predetermined threshold th2.

Note that, even in a case where the microscope 100 has three or more point light sources, it is not necessary to sequentially turn on all the point light sources to image the target S. For example, in a case where the microscope 100 has three point light sources, imaging may be performed by sequentially turning on two of the three point light sources. In this case, for example, the microscope 100 may select and turn on the farthest point light source among the plurality of point light sources.

4. Third Embodiment

In the first and second embodiments, a case where the flat region SAB is acquired from the captured image acquired by the acquisition unit 221 has been described. In addition to the above example, the information processing device 200A may acquire the flat region SAB after performing smoothing processing on the captured image. Therefore, in a third embodiment, an example in which an information processing device 200A performs the smoothing processing before acquiring the flat region SAB from the captured image will be described. Note that the information processing device 200A according to the third embodiment has the same configuration and is operated in the same manner as the information processing device 200A according to the first embodiment except for an operation of a region acquisition unit 225, and thus, is denoted by the same reference sign, and a part of description thereof will be omitted.

Figure 17:
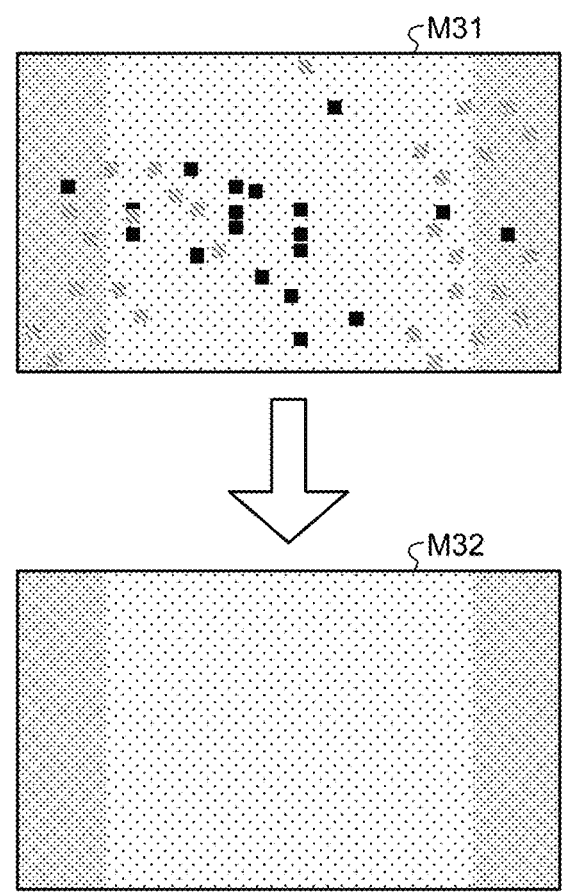
FIG. 17 is a diagram for describing smoothing processing performed by a region acquisition unit according to a third embodiment of the present disclosure.

FIG. 17 is a diagram for describing the smoothing processing performed by the region acquisition unit 225 according to the third embodiment of the present disclosure.

As illustrated in FIG. 17, a captured image M31 acquired by an acquisition unit 221 includes a local unevenness and noise of the target S. Note that the local unevenness of the target S is a depth information calculation target of a depth calculation unit 223.

In a case where the region acquisition unit 225 tries to perform threshold determination on the captured image M31 illustrated in FIG. 17 in units of pixels, accuracy in acquiring the flat region SAB is deteriorated due to an influence of the above-described unevenness and noise.

Therefore, the region acquisition unit 225 performs the smoothing processing on the captured image M31 before performing the threshold determination to acquire the flat region SAB, and generates a smoothing image M32 as illustrated on the lower side of FIG. 17. Specifically, the region acquisition unit 225 generates the smoothing image M32 by applying a low-pass filter to the captured image M31. The region acquisition unit 225 performs the threshold determination on the smoothing image M32 to generate the mask image M12 illustrated in FIG. 8.

For example, the region acquisition unit 225 compares the generated mask image M12 with the captured image M31, and extracts pixels in which the mask image M12 is white in the same coordinates from the captured image M31, thereby acquiring the flat region SAB in the captured image M31.

As described above, the region acquisition unit 225 generates the mask image M12 based on the smoothing image M32, such that the mask image M12 can be generated while reducing the influence of the fine unevenness and noise of the captured image M31. Furthermore, the region acquisition unit 225 acquires the flat region SAB of the captured image M31 by using the mask image M12, such that the flat region SAB including the local unevenness can be extracted, and the depth of the target S can be accurately calculated.

Note that, as described in the second embodiment, in a case where the acquisition unit 221 acquires a plurality of captured images, the region acquisition unit 225 performs the smoothing processing on all the acquired captured images. As a result, the information processing device 200A can suppress a decrease of the accuracy in acquiring the flat region SAB, and can improve the accuracy in shape measurement.

5. Fourth Embodiment

In the first and second embodiments, a case where the region acquisition unit 225 acquires the flat region SAB by performing the threshold determination on the luminance value of the pixel has been described. In addition to the above example, the information processing device 200A may acquire the flat region by dividing the captured image into a plurality of blocks. Therefore, in a fourth embodiment, an example in which an information processing device 200A divides a captured image into a plurality of blocks will be described. Note that the information processing device 200A according to the fourth embodiment has the same configuration and is operated in the same manner as the information processing device 200A according to the first embodiment except for an operation of a region acquisition unit 225, and thus, is denoted by the same reference sign, and a part of description thereof will be omitted.

Figure 18:
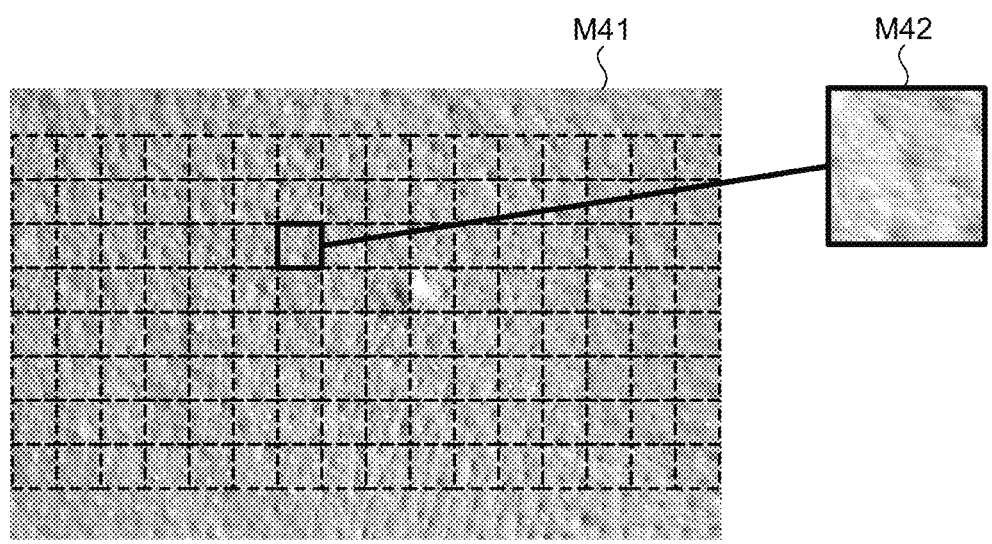
FIG. 18 is a diagram for describing acquisition of a flat region by a region acquisition unit according to a fourth embodiment of the present disclosure.

FIG. 18 is a diagram for describing acquisition of the flat region by the region acquisition unit 225 according to the fourth embodiment of the present disclosure.

As illustrated in FIG. 18, the region acquisition unit 225 divides a captured image M41 acquired by an acquisition unit 221 into, for example, a plurality of blocks, and acquires one divided block M42 as the flat region. Note that the region acquisition unit 225 determines a size of the block based on information regarding a microscope 100, and divides the captured image M41 into blocks of the determined size.

Figure 19:
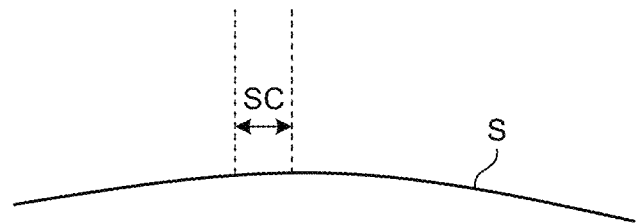
FIG. 19 is a diagram for describing acquisition of the flat region by the region acquisition unit according to the fourth embodiment of the present disclosure.

As illustrated in FIG. 19, even in a case where variation in shape of the target S is large in the entire captured image M41, a local region SC can be regarded as being substantially flat. Note that FIG. 19 is a diagram for describing acquisition of the flat region by the region acquisition unit 225 according to the fourth embodiment of the present disclosure.

For example, in a case where the target S is human skin, when an area of the target S is empirically 5 mm×5 mm or less, the region may be a flat surface that satisfies Assumptions 1 and 2 described above. Therefore, for example, the region acquisition unit 225 divides the captured image M41 into blocks of 5 mm×5 mm or less. As described above, the actual length P [μm] per pixel of the captured image is calculated based on the focal length f [mm] of a sensor 150, the length d [mm] of the housing (head-mounted portion 10), and the pixel pitch p [μm] of the sensor 150.

For example, as described above, in a case where the captured image M41 is divided into blocks of 5 mm×5 mm or less, a width w [pixel] of the block is w=5000/P=5000f/(d×p). Specifically, in a case where the focal length f of the sensor 150 is 16 [mm], the length d of the head-mounted portion 10 is 100 [mm], and the pixel pitch p of the sensor 150 is 5 [μm], the length P per pixel is P=31.25 [μm].

Therefore, in a case where the captured image M41 is divided into blocks of 5 mm×5 mm or less, the block size is 160×160 [pixel].

Note that a normal calculation unit 222 and a depth calculation unit 223 calculate normal information and depth information for all the divided blocks. Depth calculation processing is the same as the calculation processing illustrated in FIG. 13 except that the number of blocks (flat regions) to be calculated is different.

As described above, in the fourth embodiment, the information processing device 200A divides the captured image M41 into a plurality of blocks and calculates the depth. As a result, the information processing device 200A can acquire the flat region that satisfies Assumptions 1 and 2 in Expressions (1) to (3) described above, and can accurately calculate the depth. As described above, the information processing device 200A according to the fourth embodiment can improve the accuracy in shape measurement.

Here, the size of the block is 5 mm×5 mm, but is not limited thereto. For example, the imaging target of the microscope 100 may be other than human skin. Since the size of the block that can be regarded as flat varies depending on the imaging target, the size of the block may be different depending on the imaging target.

For example, in a case where the microscope 100 images a plurality of types of targets, a table in which the type of the imaging target is associated with an appropriate block size is stored in a storage unit 230. In this case, the information processing device 200A selects the size of the block according to the type of the imaging target. Alternatively, the user may designate the size of the block. As described above, the size of the block is not limited to the above-described example, and various sizes can be selected.

6. Fifth Embodiment

In the fourth embodiment, a case where the region acquisition unit 225 acquires the flat region by dividing the captured image into blocks has been described. In addition to the above example, the information processing device 200A may acquire the flat region according to a contrast value of the divided block. Therefore, in a fifth embodiment, an example in which an information processing device 200A acquires the flat region according to a contrast value of a divided block will be described. Note that the information processing device 200A according to the fifth embodiment has the same configuration and is operated in the same manner as the information processing device 200A according to the fourth embodiment except for an operation of a region acquisition unit 225, and thus, is denoted by the same reference sign, and a part of description thereof will be omitted.

Figure 20:
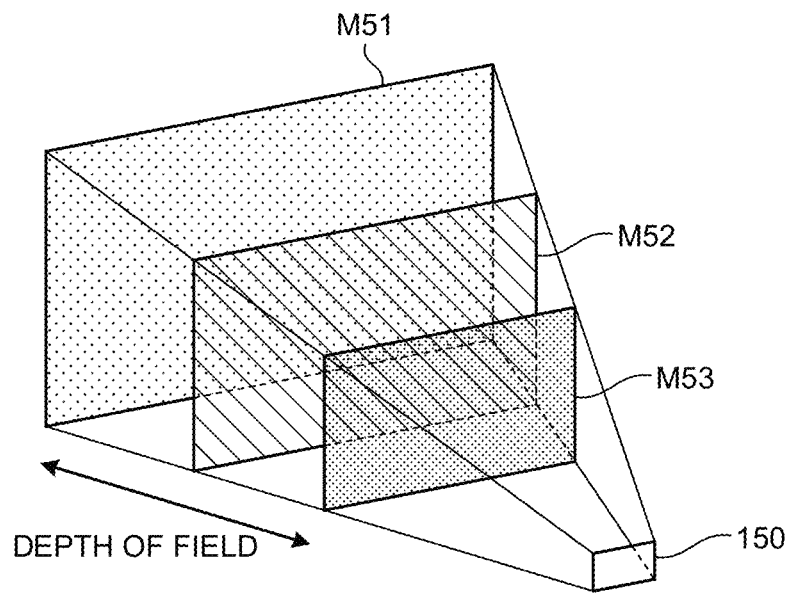
FIG. 20 is a diagram for describing a depth of field of a sensor.

FIG. 20 is a diagram for describing a depth of field of a sensor 150. The sensor 150 (camera) has a depth of field (a range of a depth at which a subject can be imaged without blurring) corresponding to a diaphragm of a lens. In an optical system of the camera, there is a focal length f at which the subject can be clearly imaged with the highest resolution by focusing. For example, a plane M52 illustrated in FIG. 20 is a focused plane, that is, a plane which is in focus and on which the subject can be clearly imaged with the highest resolution. A range from a plane M53 to a plane M51 is a depth range (the depth of field) in which the subject can be imaged without blurring.

Figure 21:
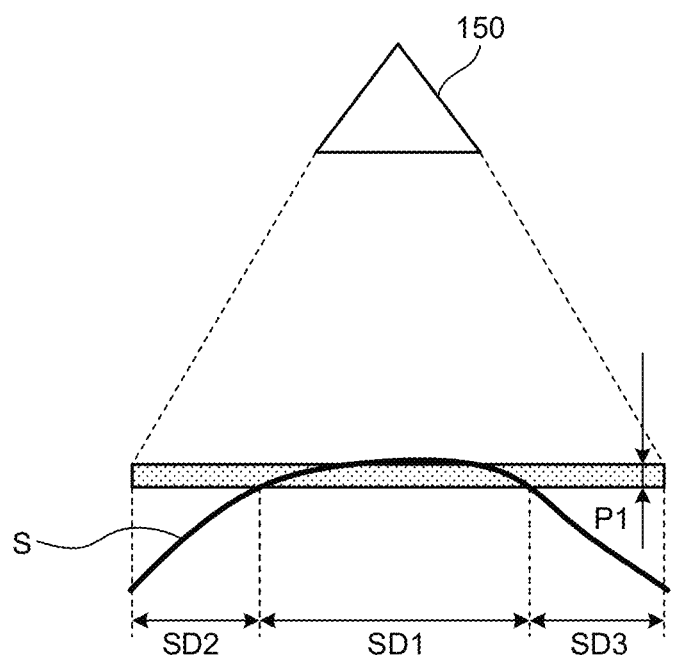
FIG. 21 is a diagram for describing acquisition of a flat region by a region acquisition unit according to a fifth embodiment of the present disclosure.

In a case where the head-mounted portion 10 is brought into contact with the target S to perform imaging as in the microscope 100, a distance to the target S becomes short, and thus, the amount of light incident on the sensor 150 becomes small. Therefore, in order to increase the amount of light incident on the sensor 150 as much as possible, imaging is performed in state in which a diaphragm value F is made small, that is, the diaphragm is opened, in the microscope 100. Therefore, a depth of field P1 becomes small as illustrated in FIG. 21. Note that FIG. 21 is a diagram for describing acquisition of the flat region by a region acquisition unit 225 according to the fifth embodiment of the present disclosure.

As illustrated in FIG. 21, since the depth of field P1 of the microscope 100 is small, the target S included in the depth of field P1, that is, a surface SD1 of the target S that has substantially the same distance from the sensor 150 in a rough shape can be imaged without blurring. On the other hand, the target S that is not included in the depth of field P1, that is, surfaces SD2 and SD3 having different distances from the sensor 150 from the surface SD1 are imaged in a state of being blurred.

Figure 22:
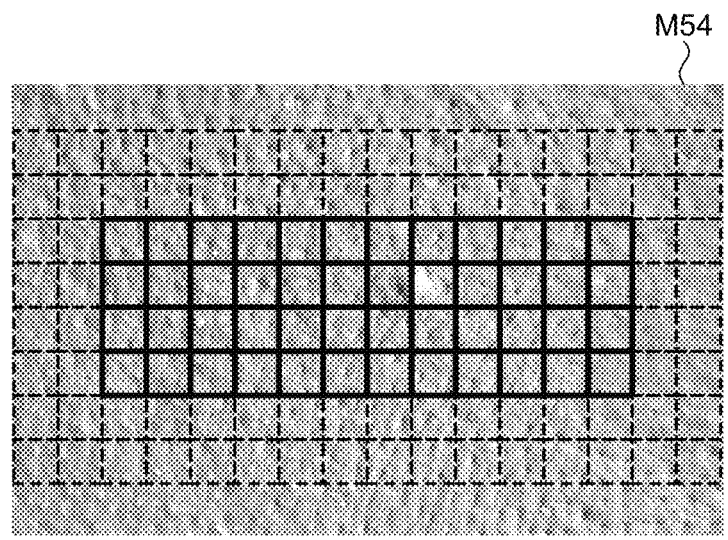
FIG. 22 is a diagram for describing acquisition of the flat region by the region acquisition unit according to the fifth embodiment of the present disclosure.

Therefore, the region acquisition unit 225 acquires an imaged region included in the depth of field P1 as the flat region. The region acquisition unit 225 acquires the flat region by acquiring a focused and non-blurred region from the captured image. This will be described with reference to FIG. 22. FIG. 22 is a diagram for describing acquisition of the flat region by the region acquisition unit 225 according to the fifth embodiment of the present disclosure.

The region acquisition unit 225 divides a captured image M54 acquired by an acquisition unit 221 into a plurality of blocks. Note that a size of the block to be divided here may be the same as or different from the size of the block of the fourth embodiment described above.

Subsequently, the region acquisition unit 225 calculates a contrast value for each divided block. The contrast value contrast is a value obtained by an expression contrast= (Lmax−Lmin)/(Lmax+Lmin). Note that Lmax is the maximum value of a luminance value L in the block, and Lmax=max(L(x,y)). Further, Lmin is the minimum value of the luminance value L in the block, and Lmin=min(L(x,y)).

An imaged region that is in focus and is not blurred has a high contrast value contrast, and an imaged region that is not in focus and is blurred has a low contrast value contrast. Therefore, the region acquisition unit 225 acquires the flat region based on the calculated contrast value contrast. Specifically, the region acquisition unit 225 compares the calculated contrast value contrast with a threshold th3 for each block. As illustrated in FIG. 22, the region acquisition unit 225 extracts a block whose contrast value contrast is equal to or more than the threshold th3 as the flat region for which the depth calculation is to be performed.

A normal calculation unit 222 and a depth calculation unit 223 calculate normal information and depth information of the flat region acquired by the region acquisition unit 225. A calculation method is the same as that of the first embodiment. Note that the normal calculation unit 222 and the depth calculation unit 223 may calculate the normal information and the depth information in units of blocks. Alternatively, the normal calculation unit 222 and the depth calculation unit 223 may calculate the normal information and the depth information collectively for the region extracted as the flat region by the region acquisition unit 225, that is, a plurality of blocks whose contrast values contrast are equal to or more than the threshold th3.

As described above, in the fifth embodiment, the information processing device 200A divides the captured image M54 into a plurality of blocks. The information processing device 200A acquires the flat region according to the contrast value contrast calculated for each divided block.

As described above, the information processing device 200A acquires the flat region according to the contrast value contrast of the captured image M54, thereby calculating the depth in the flat region that satisfies Assumptions 1 and 2 in Expressions (1) to (3) described above. As a result, the information processing device 200A according to the fifth embodiment can improve the accuracy in shape measurement.

7. Sixth Embodiment

In the fifth embodiment, a case where the region acquisition unit 225 divides one captured image into a plurality of blocks and acquires the flat region according to the contrast value of each divided block has been described. In addition to the above example, the information processing device 200A may divide each of a plurality of captured images having different subject depths into a plurality of blocks and acquire the flat region according to the contrast value of each divided block. Therefore, in a sixth embodiment, an example in which an information processing device 200A acquires the flat region according to a contrast value of each block of each of a plurality of captured images will be described. Note that the information processing device 200A according to the sixth embodiment has the same configuration and is operated in the same manner as the information processing device 200A according to the fifth embodiment except for operations of an acquisition unit 221 and a region acquisition unit 225, and thus, is denoted by the same reference sign, and a part of description thereof will be omitted.

Figure 23:
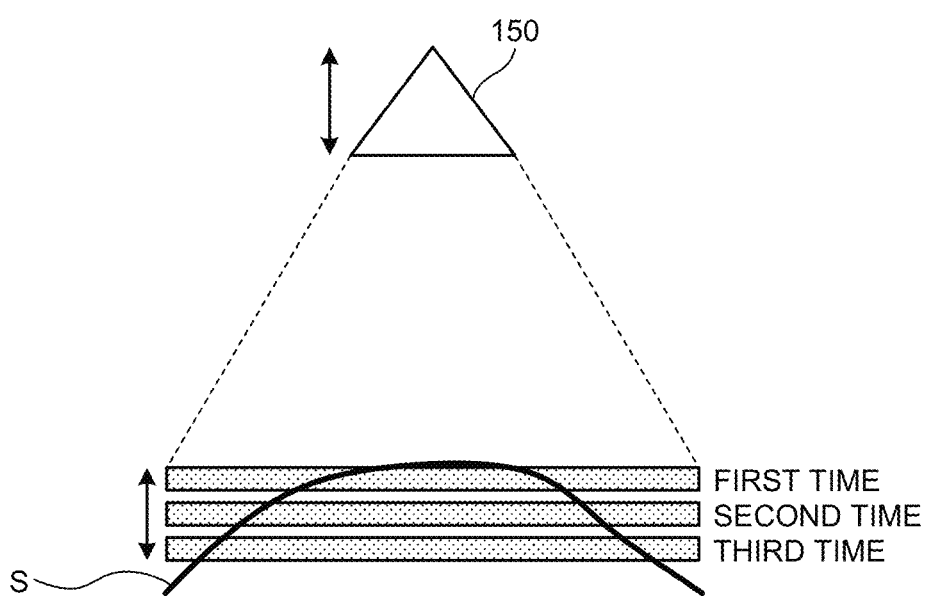
FIG. 23 is a diagram for describing a plurality of captured images acquired by an acquisition unit according to a sixth embodiment of the present disclosure.

FIG. 23 is a diagram for describing a plurality of captured images acquired by the acquisition unit 221 according to the sixth embodiment of the present disclosure. The acquisition unit 221 acquires a plurality of captured images having different subject depths. As illustrated in FIG. 23, a microscope 100 acquires a plurality of captured images having different subject depths (focus planes) by moving a sensor 150 of the microscope 100. In the example of FIG. 23, the microscope 100 captures three captured images by capturing the target S three times while moving the sensor 150 up and down. For example, at the first time imaging, the microscope 100 first captures a captured image whose subject depth is closest to the sensor 150, and at the third time imaging, the microscope 100 captures a captured image whose subject depth is farthest from the sensor 150. For example, at the second time imaging, the microscope 100 acquires a captured image whose subject depth is located between those of the first time imaging and the second time imaging.

Note that the subject depth and the number of captured images illustrated in FIG. 23 are examples, and the present invention is not limited thereto. For example, the microscope 100 may capture two or four or more captured images. Furthermore, a range of the subject depth at the time of each imaging may be continuous or partially overlapped.

The acquisition unit 221 controls, for example, the microscope 100 to acquire captured images M61 to M63 having different subject depths.

Figure 24:
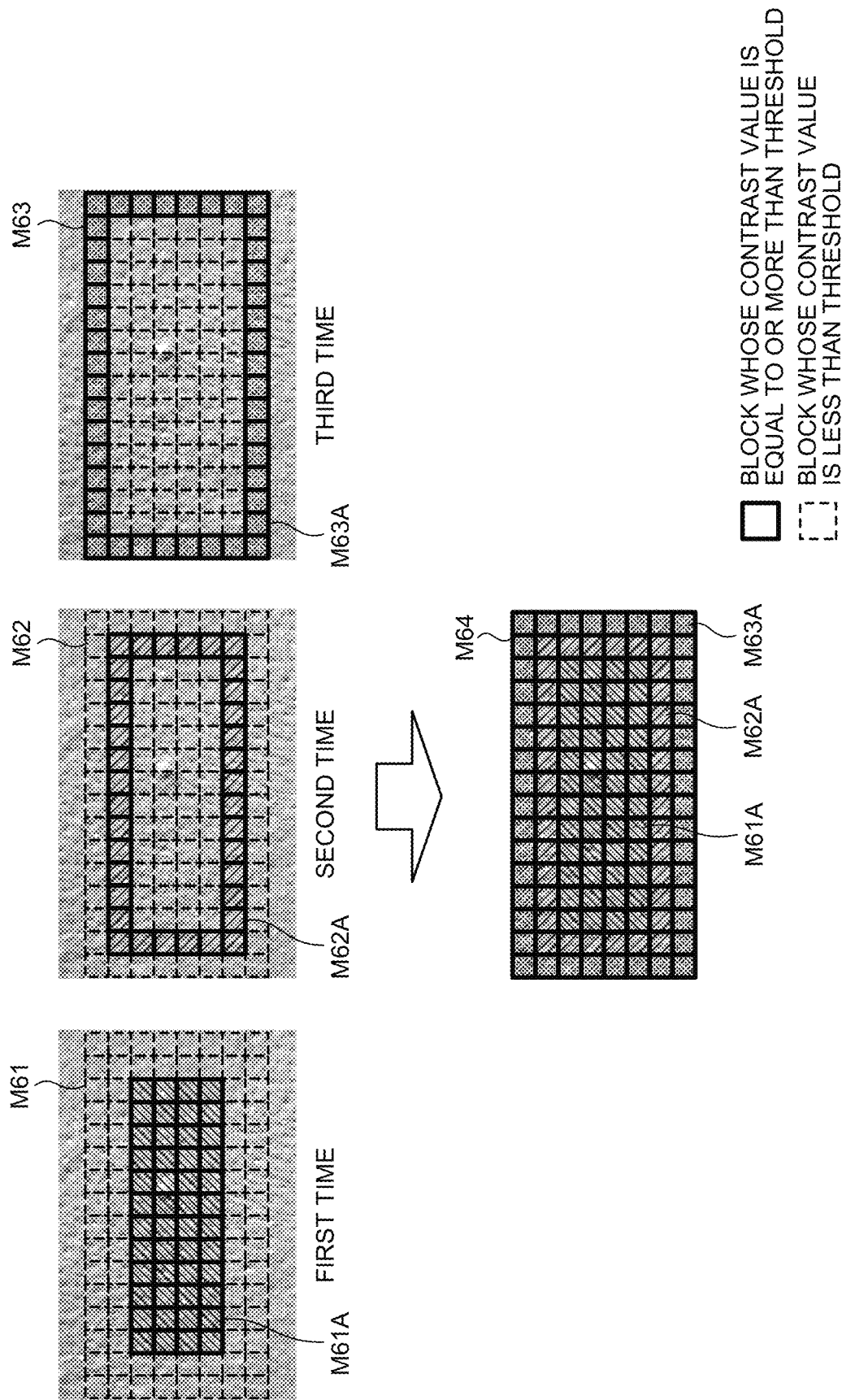
FIG. 24 is a diagram for describing acquisition of a flat region by a region acquisition unit according to the sixth embodiment of the present disclosure.

FIG. 24 is a diagram for describing acquisition of the flat region by the region acquisition unit 225 according to the sixth embodiment of the present disclosure. Here, the acquisition unit 221 causes the microscope 100 to capture captured images having different subject depths as illustrated in FIG. 23, thereby acquiring the captured images M61 to M63 as illustrated in FIG. 24.

The region acquisition unit 225 divides each of the captured images M61 to M63 into blocks. The region acquisition unit 225 calculates a contrast value contrast for each divided block. The region acquisition unit 225 compares the contrast value contrast of the calculated block with the threshold th3, and extracts a block whose contrast value contrast is equal to or more than the threshold th3 as the flat region.

For example, in FIG. 24, the region acquisition unit 225 extracts, from the captured image M61, a region M61A including a block whose contrast value contrast is equal to or more than the threshold th3 in the captured image M61. Similarly, the region acquisition unit 225 extracts, from the captured image M62, a region M62A including a block whose contrast value contrast is equal to or more than the threshold th3 in the captured image M62. Similarly, the region acquisition unit 225 extracts, from the captured image M63, a region M63A including a block whose contrast value contrast is equal to or more than the threshold th3 in the captured image M63.

Finally, the region acquisition unit 225 combines the extracted regions M61A to M63A to generate an image M64 including the flat region. In other words, the region acquisition unit 225 generates the image M64 by combining the focused and non-blurred regions of the captured images M61 to M63.

Note that processing performed by a normal calculation unit 222 and a depth calculation unit 223 on the image M64 as the flat region is the same as that in the fifth embodiment.

As described above, the information processing device 200A according to the sixth embodiment acquires a plurality of captured images having different subject depths. The information processing device 200A divides each of the plurality of acquired captured images into a plurality of blocks. The information processing device 200A acquires the flat region according to the contrast value contrast of each divided block.

As a result, the information processing device 200A acquires the flat region according to the contrast value contrast, thereby calculating the depth in the flat region that satisfies Assumptions 1 and 2 in Expressions (1) to (3) described above. Furthermore, the information processing device 200A can expand the flat region according to the contrast value contrast by acquiring the flat region from the plurality of captured images.

Note that, here, the region acquisition unit 225 combines the regions M61A to M63A, but the present invention is not limited thereto. For example, the normal calculation unit 222 and the depth calculation unit 223 may calculate normal information and depth information for each of the regions M61A to M63A, respectively, and for example, when a display control unit 224 causes a display unit to display the result, the result of combining the regions M61A to M63A may be displayed.

8. Seventh Embodiment

In the above-described first to sixth embodiments, a case where the region acquisition unit 225 acquires the flat region from the captured image has been described. In addition to the above example, a high frequency component may be extracted from the normal information calculated by the normal calculation unit 222. Therefore, in a seventh embodiment, an example of extracting a high frequency component from normal information and calculating depth information will be described.

Figure 25:
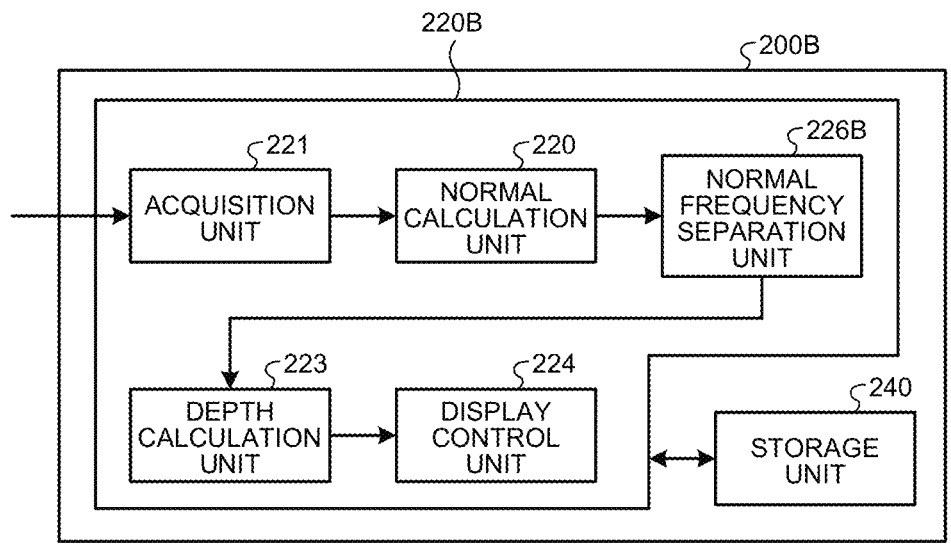
FIG. 25 is a diagram illustrating an example of a configuration of an information processing device according to a seventh embodiment of the present disclosure.

FIG. 25 is a diagram illustrating an example of a configuration of an information processing device 200B according to the seventh embodiment of the present disclosure. The information processing device 200B illustrated in FIG. 25 has the same components as those of the information processing device 200A illustrated in FIG. 6 except that a control unit 220B does not include the region acquisition unit 225 and includes a normal frequency separation unit 226B.

A normal calculation unit 222 calculates normal information in each pixel of a captured image acquired by an acquisition unit 221.

The normal frequency separation unit 226B separates a high frequency component (hereinafter, also referred to as a normal high frequency) from the normal information. Here, as described above, depth information to be calculated by a depth calculation unit 223 is information regarding a local unevenness of the target S. In other words, the depth information calculated by the depth calculation unit 223 is a high frequency component of the shape of the surface of the target S and does not include a low frequency component. The normal frequency separation unit 226 removes the low frequency component, which is the normal information of the rough shape, from the normal information to generate the normal high frequency. Since the normal high frequency does not include the low frequency component (the normal information of the rough shape), the normal high frequency satisfies Assumptions 1 and 2 of Expressions (1) to (3) described above.

Figure 26:
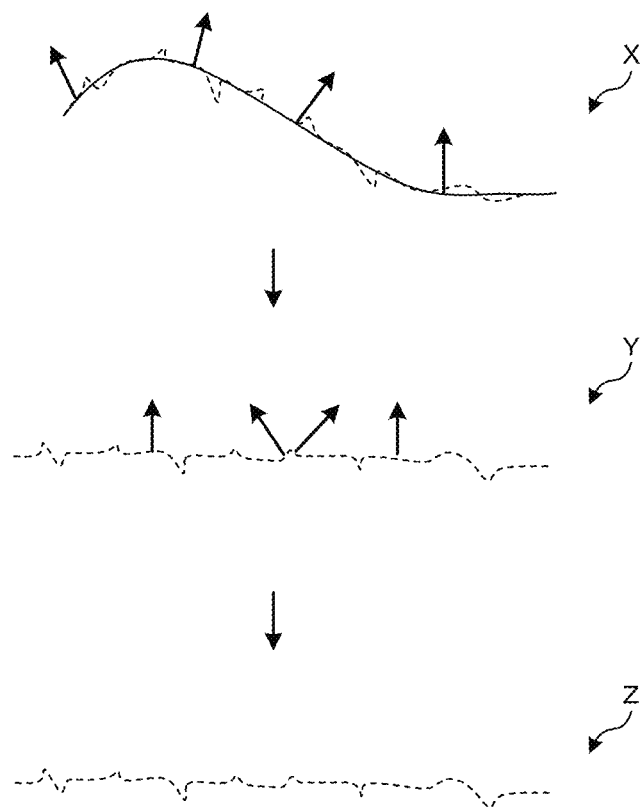
FIG. 26 is a diagram for describing frequency separation performed by a normal frequency separation unit according to the seventh embodiment of the present disclosure.

FIG. 26 is a diagram for describing frequency separation performed by the normal frequency separation unit 226B according to the seventh embodiment of the present disclosure.

For example, it is assumed that normal information X as illustrated on the upper side of FIG. 26 is input to the normal frequency separation unit 226B. Note that, in FIG. 26, the actual surface of the target S is indicated by a dotted line, the rough shape of the surface of the target S is indicated by a solid line, and the normal of the surface of the target S is indicated by an arrow.

In this case, the normal frequency separation unit 226B separates the high frequency component and the low frequency component of the normal information by using, for example, a convolution filter F(X), and extracts a normal high frequency Y illustrated on the middle side of FIG. 26. Note that the convolution filter F(X) is a filter designed in advance to extract the high frequency component when the normal information is input.

The depth calculation unit 223 can calculate depth information Z (see the lower side of FIG. 26) in a state of satisfying Assumptions 1 and 2 by performing the transform on the normal high frequency separated by the normal frequency separation unit 226B using Expressions (1) to (3) and the like described above.

In this manner, the information processing device 200B extracts the high frequency component from the normal information and calculates the depth information based on the extracted high frequency component.

As a result, the information processing device 200B can perform the transform using Expressions (1) to (3) and the like described above in a state of satisfying Assumptions 1 and 2, and thus, it is possible to suppress a decrease of accuracy in calculating the depth information. Therefore, the information processing device 200B can improve the accuracy in shape measurement as compared with a case where the frequency separation is not performed.

9. Eighth Embodiment

In the seventh embodiment, a case where the depth information is calculated from the high frequency component of the normal information has been described. In addition to the above example, the depth information may be calculated using the low frequency component in addition to the high frequency component of the normal information. Therefore, in an eighth embodiment, an example in which depth information is calculated by separating a high frequency component and a low frequency component from normal information will be described.

Figure 27:
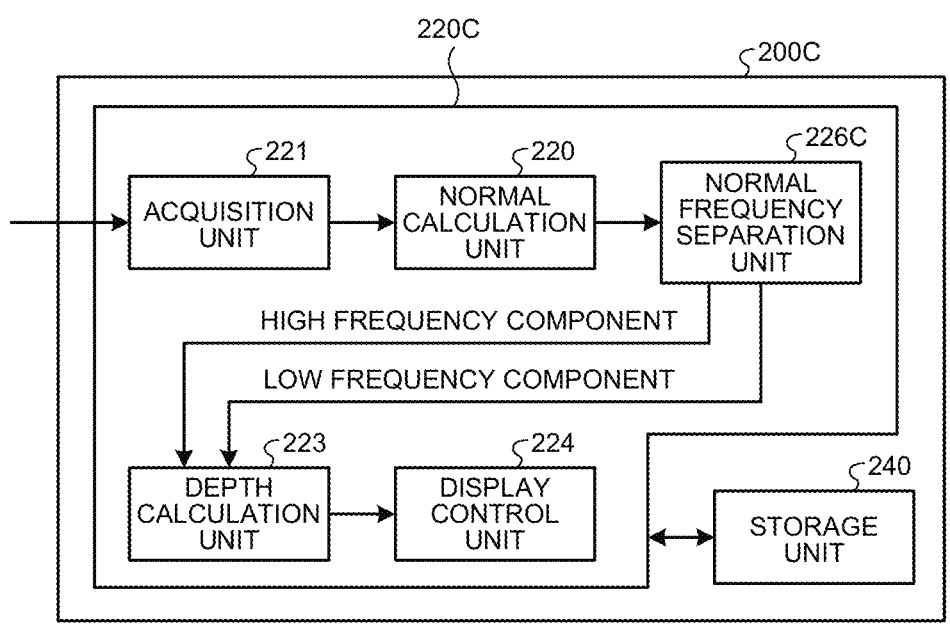
FIG. 27 is a diagram illustrating an example of a configuration of an information processing device according to an eighth embodiment of the present disclosure.

FIG. 27 is a diagram illustrating an example of a configuration of an information processing device 200C according to the eighth embodiment of the present disclosure. The information processing device 200C illustrated in FIG. 27 includes the same components as those of the information processing device 200B illustrated in FIG. 25 except for a normal frequency separation unit 226C and a depth calculation unit 223C of a control unit 220C.

The normal frequency separation unit 226C separates the high frequency component and the low frequency component (hereinafter, also referred to as a normal low frequency) from the normal information, and outputs each of the high frequency component and the low frequency component to the depth calculation unit 223C. As described above, a local unevenness of the target S contributes to the high frequency component of the normal information. In addition, the rough shape of the target S contributes to the low frequency component of the normal information. This will be described with reference to FIGS. 28A, 28B, 28C, and 28D.

FIGS. 28A, 28B, 28C, and 28D are diagrams for describing frequency separation performed by the normal frequency separation unit 226C according to the eighth embodiment of the present disclosure.

Figure 28:
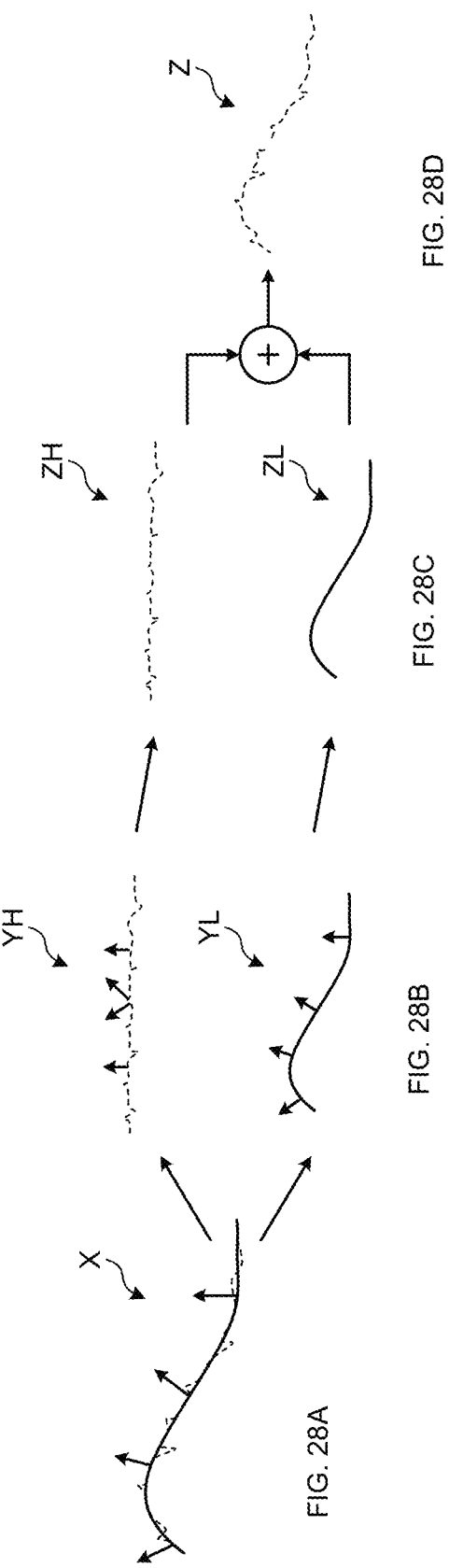
FIGS. 28A, 28B, 28C, and 28D are diagrams for describing frequency separation performed by a normal frequency separation unit according to the eighth embodiment of the present disclosure.

For example, it is assumed that normal information X as illustrated in FIG. 28A is input to the normal frequency separation unit 226C. Note that, in FIGS. 28A, 28B, 28C, and 28D, the actual surface of the target S is indicated by a dotted line, the rough shape of the surface of the target S is indicated by a solid line, and the normal of the surface of the target S is indicated by an arrow.

In this case, the normal frequency separation unit 226C extracts the high frequency component of the normal information by using, for example, a convolution filter F (X), and extracts a normal high frequency YH=F(X). As illustrated on the upper side of FIG. 28B, the surface shape represented by the normal high frequency YH is a shape in which the rough shape (normal low frequency YL) is removed and the local unevenness is present on the flat surface. Note that the convolution filter F(X) is a filter designed in advance to extract the high frequency component when the normal information is input.

In addition, the normal frequency separation unit 226C extracts the normal low frequency YL by subtracting the normal high frequency YH from the normal information X. That is, the normal frequency separation unit 226C extracts the normal low frequency YL by calculating the normal low frequency YL=X−YH=X−F(X). As illustrated on the lower side of FIG. 28B, the surface shape represented by the normal low frequency YL is a rough shape from which the local unevenness is removed.Z The depth calculation unit 223C performs the transform on each of the normal high frequency YH and the normal low frequency YL by using an expression, and calculates a high frequency component ZH (hereinafter, also referred to as a depth high frequency) and a low frequency component ZL (hereinafter, also referred to as a depth low frequency) of the depth information as illustrated in FIG. 28C.

Here, since the normal high frequency YH satisfies Assumptions 1 and 2 of the transform using an expression as described above, the depth calculation unit 223C can accurately calculate the depth high frequency ZH.

In addition, the depth calculation unit 223C calculates the depth low frequency ZL by performing the transform on the normal low frequency YL with each of $\lambda$ and $\mu$ set to 0 ($\lambda=0$ and $\mu=0$) in Expressions (1) to (3) described above. As described above, by setting a coefficient of the cost term to 0, the depth low frequency ZL can be calculated in a state in which Assumptions 1 and 2 are excluded. Note that the normal low frequency YL is the low frequency component of the normal information X from which the normal high frequency YH has been removed, and is normal information indicating a state in which a local unevenness has been removed from the shape of the surface of the target S. Therefore, the depth calculation unit 223C can accurately calculate the depth low frequency ZL even when the transform is performed on the normal low frequency YL by using an expression in a state in which Assumptions 1 and 2 are excluded.

The depth calculation unit 223C calculates the depth information Z illustrated in FIG. 28D by combining the calculated depth high frequency ZH and depth low frequency ZL.

In this manner, the information processing device 200C performs frequency separation on the normal information calculated from the captured image. The information processing device 200C calculates the depth information for each separated frequency, combines pieces of calculated depth information, and calculates the depth information of the target S.

As a result, the information processing device 200C can calculate the depth of the rough shape in addition to the depth of the local unevenness. Furthermore, the information processing device 200C can calculate the depth information of the target S more accurately by combining these depths.

Note that, here, the depth calculation unit 223C performs the transform on the normal low frequency YL with each of $\lambda$ and $\mu$ set to 0 ($\lambda=0$ and $\mu=0$) in Expressions (1) to (3) described above, but the present invention is not limited thereto. It is sufficient that the depth calculation unit 223C can calculate the depth low frequency ZL in a state in which the influence of Assumptions 1 and 2 is small, and the values of $\lambda$ and $\mu$ may be set to values that are small enough so that Assumptions 1 and 2 do not affect the calculation of the depth low frequency ZL.

10. Ninth Embodiment

Figure 29:
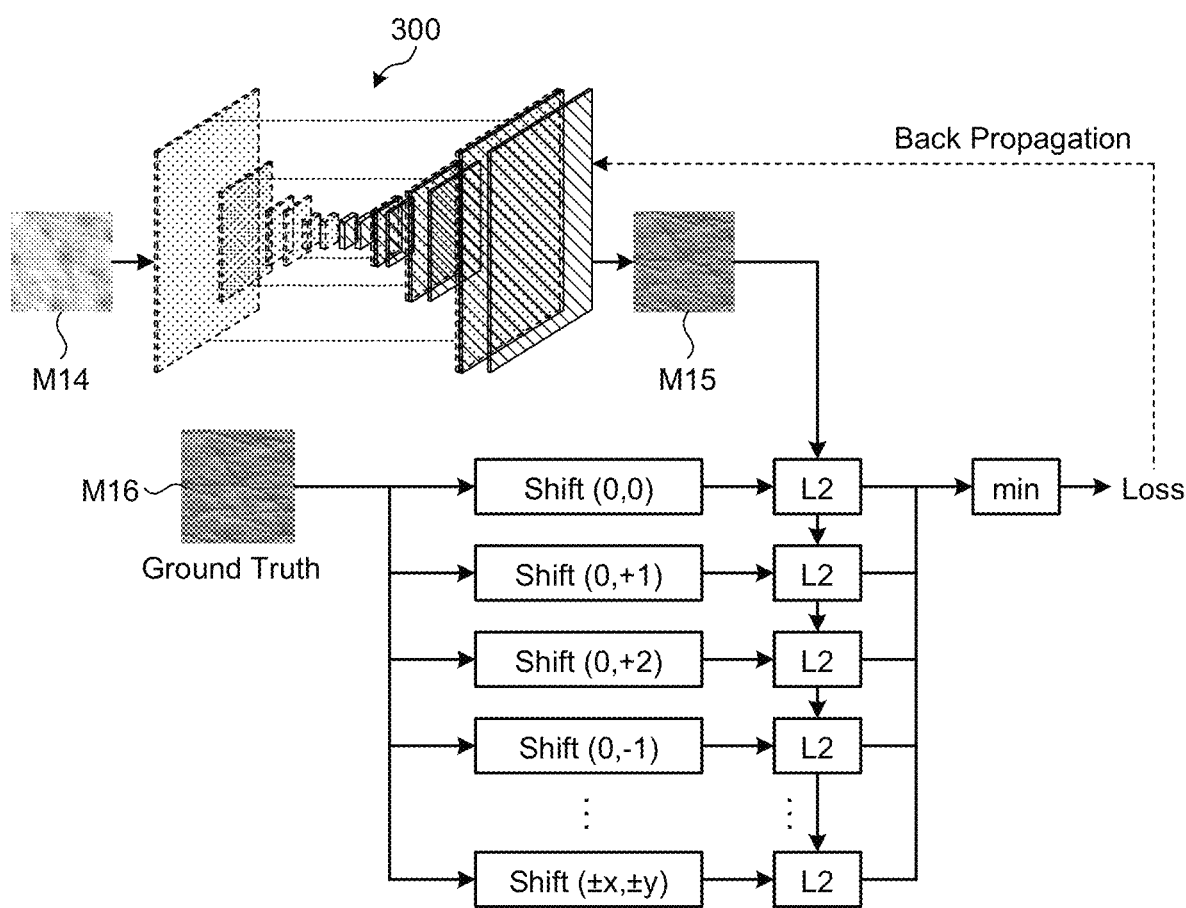
FIG. 29 is a diagram for describing a learning method for a learning machine according to a ninth embodiment.

In the first embodiment, a case where the learning machine 300 is trained using the image M16 which is the ground truth has been described. In addition to the above example, the information processing device 200A may train the learning machine 300 by using, as correct answer data, an image obtained by shifting the image M16. Therefore, in a ninth embodiment, an example in which an information processing device 200A trains a learning machine 300 by using, as correct answer data, an image obtained by shifting an image M16 will be described with reference to FIG. 29. FIG. 29 is a diagram for describing a learning method for the learning machine 300 according to the ninth embodiment.

Note that the information processing device 200A according to the ninth embodiment has the same configuration and is operated in the same manner as the information processing device 200A according to the first embodiment except for an operation of a normal calculation unit 222, and thus, is denoted by the same reference sign, and a part of description thereof will be omitted.

As described above, the normal calculation unit 222 performs learning by updating a weight of the learning machine 300 with a captured image M14 as input data and the normal image M16 as the correct answer data (ground truth). Here, the captured image M14 is captured by a device that captures an RGB image, such as a microscope 100. On the other hand, the normal image M16 is generated based on shape information measured by a device that directly measures a shape of a surface of the target S, such as a non-contact 3D measuring instrument.

As described above, in a case where an optical system of the device that acquires the input image is different from an optical system of the device that acquires the correct answer image, it becomes difficult to align the input image and the correct answer image. Therefore, an output image obtained by inputting the input image to the learning machine 300 and the correct answer image may be shifted by several pixels. As described above, when the learning machine 300 is trained in a state in which the output image and the correct answer image are shifted, the learning machine 300 that outputs a blurred output image for the input image is generated.

Therefore, as illustrated in FIG. 29, at the time of learning to determine a filter coefficient (weight) of the learning machine (CNN) 300, the normal calculation unit 222 shifts the normal image M16 in the x direction and the y direction, and calculates similarity between the shifted normal image M16 and an output image M15. Note that the normal calculation unit 222 shifts the normal image M16 in a range of 0 to ±x in the x direction and in a range of 0 to ±y in the y direction.

For example, the normal calculation unit 222 calculates a least square error between the shifted normal image M16 and the output image M15 for each shift amount. The normal calculation unit 222 updates the weight of the learning machine 300 with the minimum value of the calculated least square error as a final loss. Note that, instead of the least square error, a minimum average error between the shifted normal image M16 and the output image M15 may be calculated for each shift amount, and the minimum value of the calculated minimum average error may be used as the final loss.

In this manner, the learning machine 300 is generated by updating the weight according to the similarity between the shifted image (shifted normal image) obtained by shifting the ground truth image (normal image) and the output image M15. More specifically, the learning machine 300 is generated by updating the weight according to the similarity between each of a plurality of shifted images (also referred to as shifted normal images or correct answer candidate images) obtained by shifting the ground truth image (normal image) by different shift amounts (the different numbers of pixels) and the output image M15.

As a result, even in a case where alignment between the output image M15 and the normal image M16 of the learning machine 300 is not performed, the weight of the learning machine 300 can be updated in a state in which the two images are aligned. As a result, accuracy in training the learning machine 300 can be further improved. Furthermore, as the normal calculation unit 222 calculates the normal information by using the learning machine 300, the normal information can be calculated with higher accuracy, and the accuracy in shape measurement of the information processing device 200A can be further improved.

11. Tenth Embodiment

Figure 30:
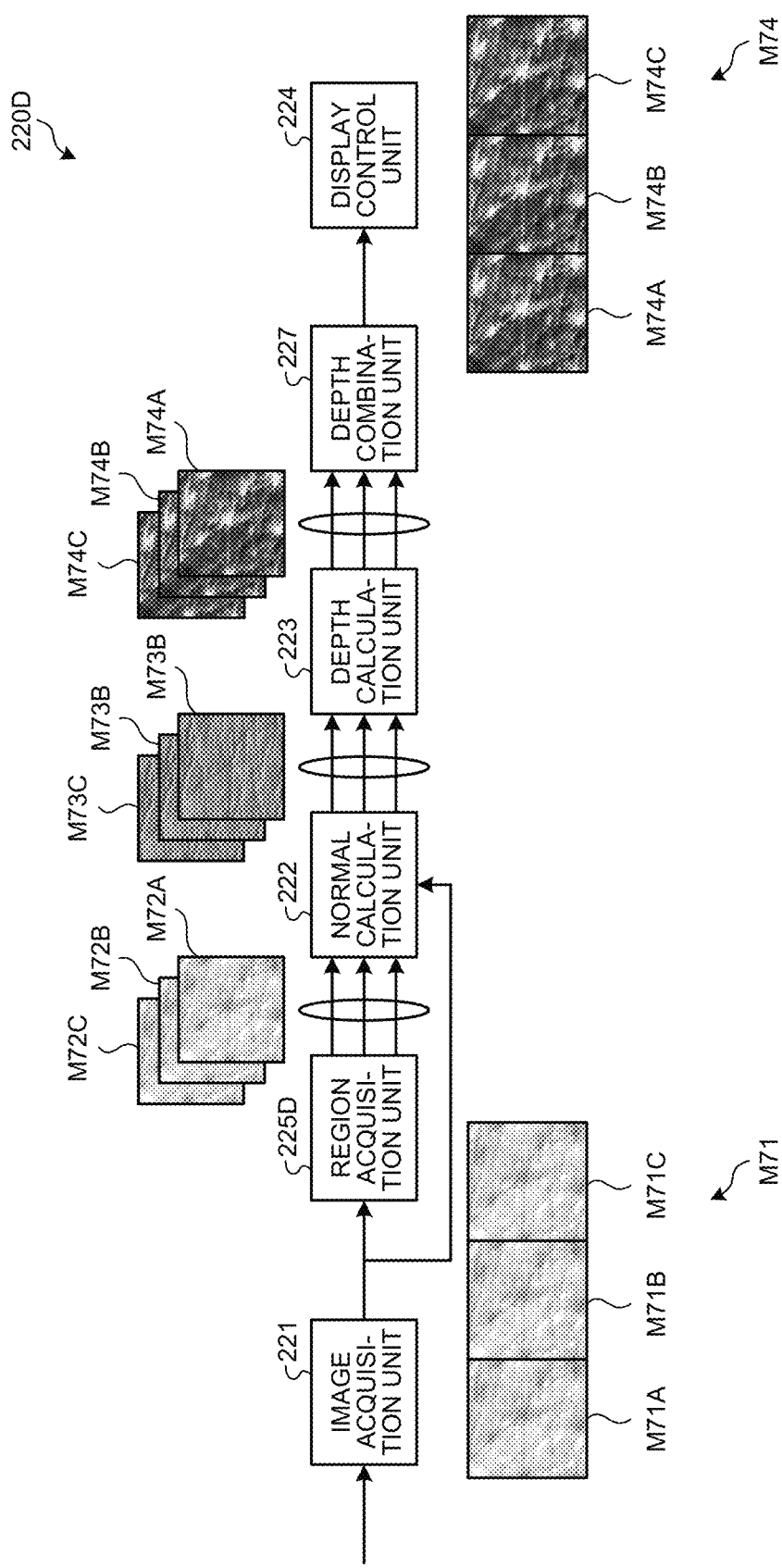
FIG. 30 is a diagram illustrating an example of a configuration of a control unit of an information processing device according to a tenth embodiment of the present disclosure.

In the above-described first embodiment, a case where the flat region is acquired from the captured image has been described. In addition to the above example, the information processing device 200A may divide a captured image into a plurality of regions and acquire the flat region for each of the divided regions. Therefore, in a tenth embodiment, an example in which an information processing device 200A divides a captured image into a plurality of regions and acquires the flat region for each of the divided regions will be described with reference to FIG. 30. FIG. 30 is a diagram illustrating an example of a configuration of a control unit 220D of the information processing device 200A according to the tenth embodiment of the present disclosure.

As illustrated in FIG. 30, the control unit 220D of the information processing device 200A is the same as the control unit 220 illustrated in FIG. 6 except that a region acquisition unit 225D is included instead of the region acquisition unit 225 and a depth combination unit 227 is further included.

As illustrated in FIG. 30, the region acquisition unit 225D divides a captured image M71 acquired by an acquisition unit 221 into three divided regions M71A to M71C. Note that the number of regions divided by the region acquisition unit 225D is not limited to three, and may be two or four or more.

The region acquisition unit 225D acquires divided flat regions M72A to M72C for each of the divided regions M71A to M71C. A normal calculation unit 222 calculates normal region images M73A to M73C based on the divided flat regions M72A to M72C, respectively, and a depth calculation unit 223 calculates depth region images M74A to M74C based on the normal region images M73A to M73C, respectively.

The depth combination unit 227 combines the depth region images M74A to M74C to generate a depth image M75, and outputs the depth image M75 to a display control unit 224.

Note that the depth combination unit 227 may combine the divided flat regions M72A to M72C or combine the normal region images M73A to M73C in addition to the depth region images M74A to M74. In addition, processing in each unit may be sequentially performed for each region or may be performed in parallel for each region.

In this manner, the information processing device 200A divides the captured image into the plurality of divided regions M71A to M71C, and acquires the divided flat regions M72A to M72C for each of the divided regions M71A to M71C. Furthermore, the information processing device 200A calculates normal information and depth information for each of the divided flat regions M72A to M72C.

As a result, a size of the captured image (region) to be processed by each unit can be reduced, a processing load can be reduced, and a processing speed can be improved.

12. Other Embodiments

The processing according to each embodiment described above may be performed in various different modes other than that in each of the embodiments described above.

In the above-described embodiments, an example in which the head-mounted portion 10 is a cylindrical portion mounted on the distal end of the microscope 100 has been described. However, the head-mounted portion 10 does not have to have a cylindrical shape as long as it is a structure for keeping the distance between the target S and the sensor 150 of the microscope 100 constant.

13. Adaptation Example

Figure 31:
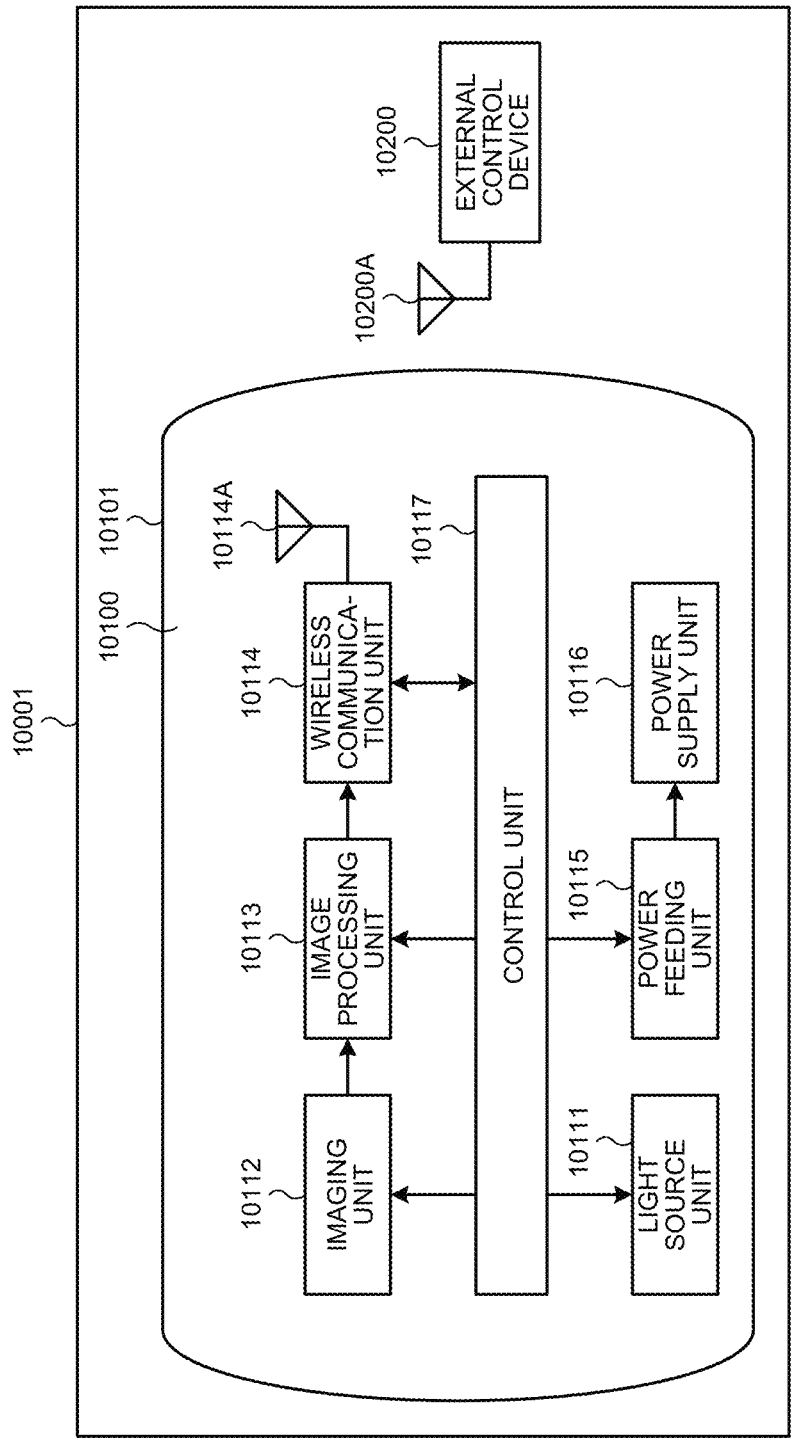
FIG. 31 is a block diagram illustrating an example of a schematic configuration of a patient in-vivo information acquisition system using a capsule endoscope to which a technology according to the present disclosure (the present technology) can be applied.

An adaptation example of the information processing devices 200A to 200C according to the first to tenth embodiments will be described with reference to FIG. 31. FIG. 31 is a block diagram illustrating an example of a schematic configuration of a patient in-vivo information acquisition system using a capsule endoscope to which a technology according to the present disclosure (the present technology) can be applied.

An in-vivo information acquisition system 10001 includes a capsule endoscope 10100 and an external control device 10200.

The capsule endoscope 10100 is swallowed by a patient at the time of examination. The capsule endoscope 10100 has an imaging function and a wireless communication function, sequentially captures an image of the inside of an organ (hereinafter, also referred to as an in-vivo image) at predetermined intervals while moving inside the organ such as the stomach or the intestines by peristaltic movement or the like until being naturally discharged from the patient, and sequentially wirelessly transmits information regarding the in-vivo image to the external control device 10200 outside the body.

The external control device 10200 integrally controls the operation of the in-vivo information acquisition system 10001. Furthermore, the external control device 10200 receives the information regarding the in-vivo image transmitted from the capsule endoscope 10100, and generates image data for displaying the in-vivo image on a display device (not illustrated) based on the received information regarding the in-vivo image.

In this manner, the in-vivo information acquisition system 10001 can obtain the in-vivo image obtained by imaging a state of the inside of the body of the patient at any time from when the capsule endoscope 10100 is swallowed to when the capsule endoscope is discharged.

Configurations and functions of the capsule endoscope 10100 and the external control device 10200 will be described in more detail.

The capsule endoscope 10100 includes a capsule-shaped housing 10101, and a light source unit 10111, an imaging unit 10112, an image processing unit 10113, a wireless communication unit 10114, a power feeding unit 10115, a power supply unit 10116, and a control unit 10117 are housed in the housing 10101.

The light source unit 10111 is implemented by a light source such as a light emitting diode (LED), for example, and irradiates an imaging field of view of the imaging unit 10112 with light.

The imaging unit 10112 includes an imaging element and an optical system including a plurality of lenses provided on the upstream side of the imaging element. Reflected light (hereinafter, referred to as observation light) of light radiated to a body tissue to be observed is collected by the optical system and is incident on the imaging element. In the imaging unit 10112, the observation light incident on the imaging element is photoelectrically converted, and an image signal corresponding to the observation light is generated. The image signal generated by the imaging unit 10112 is provided to the image processing unit 10113.

The image processing unit 10113 is implemented by a processor such as a central processing unit (CPU) or a graphics processing unit (GPU), and performs various types of signal processing on the image signal generated by the imaging unit 10112. The image processing unit 10113 provides the image signal subjected to the signal processing to the wireless communication unit 10114 as raw data.

The wireless communication unit 10114 performs predetermined processing such as modulation processing on the image signal subjected to the signal processing by the image processing unit 10113, and transmits the image signal to the external control device 10200 via an antenna 10114A. In addition, the wireless communication unit 10114 receives a control signal related to a drive control of the capsule endoscope 10100 from the external control device 10200 via the antenna 10114A. The wireless communication unit 10114 provides, to the control unit 10117, the control signal received from the external control device 10200.

The power feeding unit 10115 includes a power receiving antenna coil, a power regeneration circuit that regenerates power from a current generated in the antenna coil, a booster circuit, and the like. In the power feeding unit 10115, power is generated using a so-called non-contact charging principle.

The power supply unit 10116 is implemented by a secondary battery, and stores electric power generated by the power feeding unit 10115. In FIG. 31, an arrow or the like indicating a supply destination of power from the power supply unit 10116 is not illustrated in order to avoid complexity of the drawing, but the power stored in the power supply unit 10116 is supplied to the light source unit 10111, the imaging unit 10112, the image processing unit 10113, the wireless communication unit 10114, and the control unit 10117, and can be used for driving these units.

The control unit 10117 is implemented by a processor such as a CPU, and appropriately controls driving of the light source unit 10111, the imaging unit 10112, the image processing unit 10113, the wireless communication unit 10114, and the power feeding unit 10115 according to the control signal transmitted from the external control device 10200.

The external control device 10200 is implemented by a processor such as a CPU or a GPU, a microcomputer in which a processor and a storage element such as a memory are mixedly mounted, a control board, or the like. The external control device 10200 controls the operation of the capsule endoscope 10100 by transmitting the control signal to the control unit 10117 of the capsule endoscope 10100 via an antenna 10200A. In the capsule endoscope 10100, for example, a light irradiation condition for the observation target in the light source unit 10111 can be changed according to the control signal from the external control device 10200. Furthermore, an imaging condition (for example, a frame rate, an exposure value, or the like in the imaging unit 10112) can be changed according to the control signal from the external control device 10200. Furthermore, contents of the processing in the image processing unit 10113 and a condition (for example, a transmission interval, the number of images to be transmitted, or the like) under which the wireless communication unit 10114 transmits the image signal may be changed according to the control signal from the external control device 10200.

Furthermore, the external control device 10200 performs various types of image processing on the image signal transmitted from the capsule endoscope 10100, and generates the image data for displaying the captured in-vivo image on the display device. As the image processing, for example, various types of signal processing such as development processing (demosaic processing), high image quality processing (band emphasis processing, super-resolution processing, noise reduction processing, image stabilization processing, or the like), and enlargement processing (electronic zoom processing) can be performed alone or in combination. The external control device 10200 controls driving of the display device to display the captured in-vivo image based on the generated image data. Alternatively, the external control device 10200 may cause a recording device (not illustrated) to record the generated image data or cause a printing device (not illustrated) to print out the generated image data.

Hereinabove, an example of the in-vivo information acquisition system to which the technology according to the present disclosure can be applied has been described. The technology according to the present disclosure can be applied to, for example, the external control device 10200 among the above-described configurations. By applying the technology according to the present disclosure to the external control device 10200, it is possible to measure a shape of a surface in the body from the in-vivo image captured by the capsule endoscope 10100.

(Example of Application to Endoscopic Surgery System)

Figure 32:
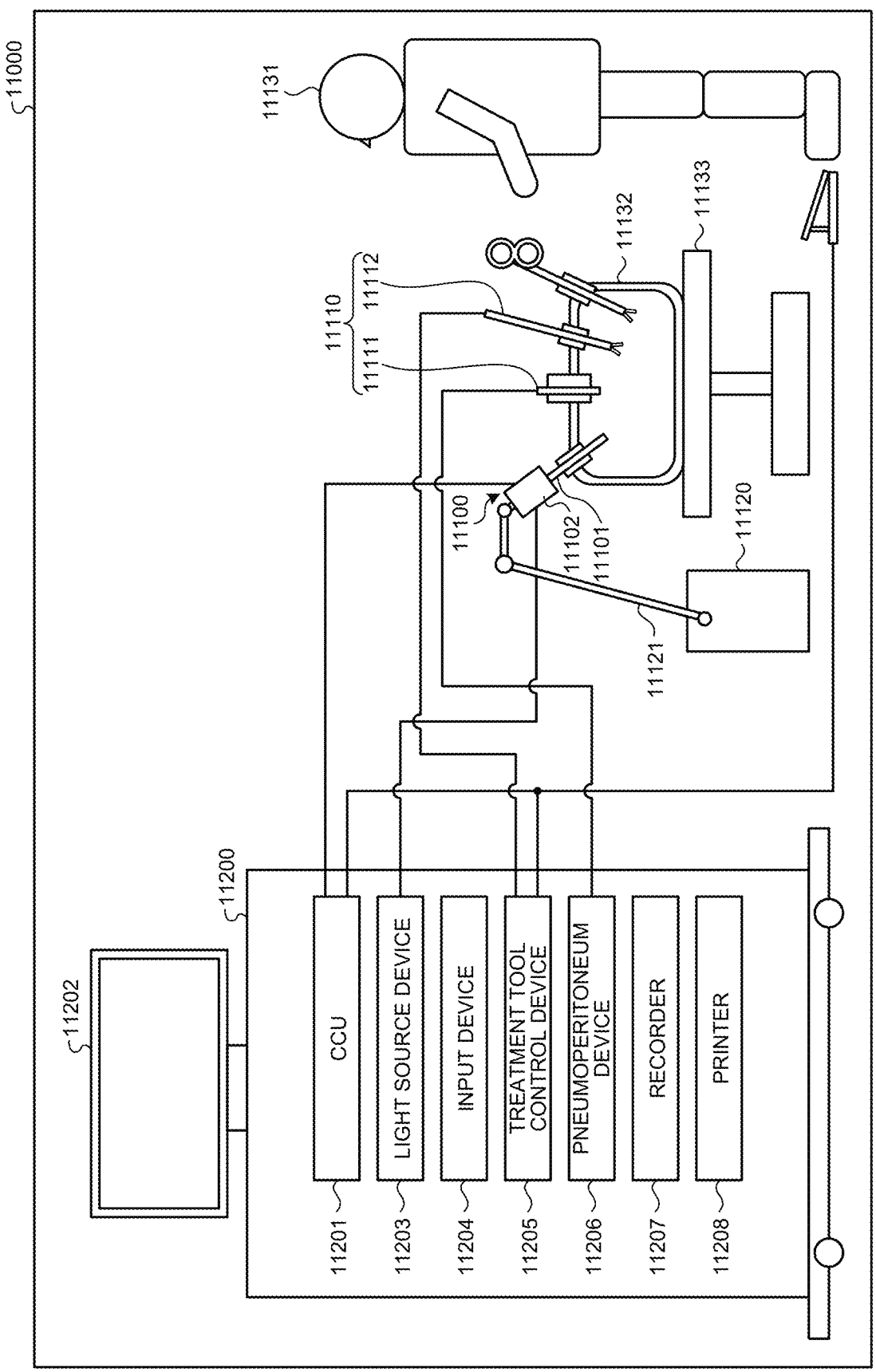
FIG. 32 is a diagram illustrating an example of a schematic configuration of an endoscopic surgery system to which the technology according to the present disclosure (the present technology) can be applied.

The technology according to the present disclosure may be further applied to an endoscopic surgical system. FIG. 32 is a diagram illustrating an example of a schematic configuration of the endoscopic surgery system to which the technology according to the present disclosure (the present technology) can be applied.

FIG. 32 illustrates a state in which an operator (doctor) 11131 is performing surgery on a patient 11132 on a patient bed 11133 by using an endoscopic surgery system 11000. As illustrated, the endoscopic surgery system 11000 includes an endoscope 11100, other surgical tools 11110 such as a pneumoperitoneum tube 11111 and an energy treatment tool 11112, a support arm device 11120 that supports the endoscope 11100, and a cart 11200 on which various devices for endoscopic surgery are mounted.

The endoscope 11100 includes a lens barrel 11101 in which a region corresponding to a predetermined length from a distal end is inserted into the body cavity of the patient 11132, and a camera head 11102 connected to a proximal end of the lens barrel 11101. In the illustrated example, the endoscope 11100 configured as a so-called rigid endoscope including the rigid lens barrel 11101 is illustrated, but the endoscope 11100 may be configured as a so-called flexible endoscope including a flexible lens barrel.

An opening portion into which an objective lens is fitted is provided at the distal end of the lens barrel 11101. A light source device 11203 is connected to the endoscope 11100, and light generated by the light source device 11203 is guided to the distal end of the lens barrel by a light guide extending inside the lens barrel 11101, and is emitted toward an observation target in the body cavity of the patient 11132 via the objective lens. Note that the endoscope 11100 may be a forward-viewing endoscope, an oblique-viewing endoscope, or a side-viewing endoscope.

An optical system and an imaging element are provided inside the camera head 11102, and reflected light (observation light) from the observation target is condensed on the imaging element by the optical system. The observation light is photoelectrically converted by the imaging element, and an electric signal corresponding to the observation light, that is, an image signal corresponding to the observation image is generated. The image signal is transmitted to a camera control unit (CCU) 11201 as raw data.

The CCU 11201 includes a CPU, a GPU, and the like, and integrally controls operations of the endoscope 11100 and a display device 11202. Furthermore, the CCU 11201 receives the image signal from the camera head 11102, and performs various types of image processing for displaying an image based on the image signal, such as development processing (demosaic processing), on the image signal.

The display device 11202 displays an image based on the image signal subjected to the image processing by the CCU 11201 under the control of the CCU 11201.

The light source device 11203 is implemented by a light source such as a light emitting diode (LED), for example, and supplies, to the endoscope 11100, irradiation light for capturing an image of a surgical site or the like.

An input device 11204 is an input interface for the endoscopic surgery system 11000. The user can input various types of information or instructions to the endoscopic surgery system 11000 via the input device 11204. For example, the user inputs an instruction to change imaging conditions (a type of the irradiation light, a magnification, a focal length, and the like) of the endoscope 11100 and the like.

A treatment tool control device 11205 controls driving of the energy treatment tool 11112 for cauterization and incision of tissue, vascular closure, or the like. A pneumoperitoneum device 11206 feeds gas into the body cavity of the patient 11132 via the pneumoperitoneum tube 11111 in order to inflate the body cavity for the purpose of securing a clear view for the endoscope 11100 and securing a working space for the operator. A recorder 11207 is a device capable of recording various types of information regarding surgery. A printer 11208 is a device capable of printing various types of information regarding surgery in various formats such as text, images, or graphs.

Note that the light source device 11203 that supplies the irradiation light to the endoscope 11100 at the time of capturing an image of the surgical site can include, for example, a white light source implemented by an LED, a laser light source, or a combination thereof. In a case where the white light source is implemented by a combination of RGB laser light sources, an output intensity and an output timing of each color (each wavelength) can be controlled with high accuracy, and thus, white balance adjustment of the captured image can be performed in the light source device 11203. Furthermore, in this case, the observation target is irradiated with laser light from each of the RGB laser light sources in a time division manner and the driving of the imaging element of the camera head 11102 is controlled in synchronization with a timing of the irradiation, such that it is also possible to capture an image corresponding to each of RGB in a time division manner. With this method, a color image can be obtained without providing a color filter in the imaging element.

Furthermore, the driving of the light source device 11203 may be controlled so as to change the intensity of light to be output every predetermined time. The driving of the imaging element of the camera head 11102 is controlled in synchronization with a timing of the change of the intensity of the light to acquire images in a time division manner, and the images are combined, such that it is possible to generate a high dynamic range image without so-called underexposure and overexposure.

Furthermore, the light source device 11203 may be configured to be able to supply light in a predetermined wavelength band corresponding to special light observation. In the special light observation, for example, so-called narrow band imaging, in which an image of a predetermined tissue such as a blood vessel in a mucosal epithelial layer is captured with high contrast by radiating light in a narrower band than irradiation light (that is, white light) at the time of normal observation, by using wavelength dependency of light absorption in a body tissue, is performed. Alternatively, in the special light observation, fluorescence observation for obtaining an image by fluorescence generated by irradiation with excitation light may be performed. In the fluorescence observation, for example, fluorescence from a body tissue can be observed by irradiating the body tissue with excitation light (autofluorescence observation), or a fluorescent image can be obtained by locally injecting a reagent such as indocyanine green (ICG) into a body tissue and irradiating the body tissue with excitation light corresponding to a fluorescence wavelength of the reagent. The light source device 11203 can be configured to be able to supply narrow band light and/or excitation light corresponding to such special light observation.

Figure 33:
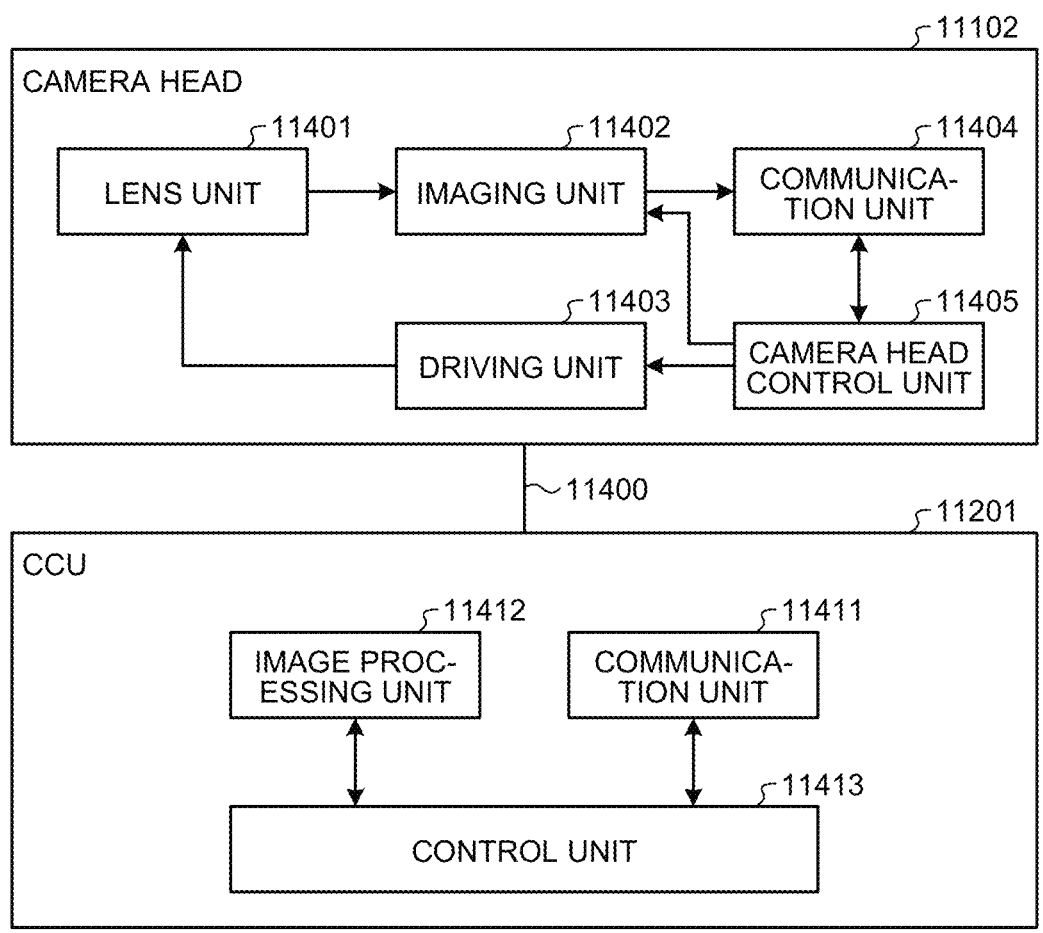
FIG. 33 is a block diagram illustrating an example of functional configurations of a camera head and a camera control unit (CCU) illustrated in FIG. 32.

FIG. 33 is a block diagram illustrating an example of functional configurations of the camera head 11102 and the CCU 11201 illustrated in FIG. 32.

The camera head 11102 includes a lens unit 11401, an imaging unit 11402, a driving unit 11403, a communication unit 11404, and a camera head control unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided at a portion at which the camera head 11102 is connected to the lens barrel 11101. The observation light taken in from the distal end of the lens barrel 11101 is guided to the camera head 11102 and is incident on the lens unit 11401. The lens unit 11401 is implemented by combining a plurality of lenses including a zoom lens and a focus lens.

The imaging unit 11402 includes the imaging element. The number of imaging elements included in the imaging unit 11402 may be one (so-called single-plate type) or plural (so-called multi-plate type). In a case where the imaging unit 11402 is configured as the multi-plate type, for example, image signals corresponding to RGB, respectively, may be generated by the respective imaging elements, and a color image may be obtained by combining the image signals. Alternatively, the imaging unit 11402 may include a pair of imaging elements for acquiring image signals for the right eye and the left eye corresponding to three-dimensional (3D) display. As the 3D display is performed, the operator 11131 can more accurately grasp a depth of a living tissue in the surgical site. Note that, in a case where the imaging unit 11402 is configured as the multi-plate type, a plurality of lens units 11401 can be provided corresponding to the respective imaging elements.

Furthermore, the imaging unit 11402 does not have to be necessarily provided in the camera head 11102. For example, the imaging unit 11402 may be provided immediately behind the objective lens inside the lens barrel 11101.

The driving unit 11403 is implemented by an actuator, and moves the zoom lens and the focus lens of the lens unit 11401 by a predetermined distance along an optical axis under the control of the camera head control unit 11405. As a result, a magnification and a focal point of the image captured by the imaging unit 11402 can be appropriately adjusted.

The communication unit 11404 is implemented by a communication device for transmitting and receiving various types of information to and from the CCU 11201. The communication unit 11404 transmits the image signal obtained from the imaging unit 11402 as raw data to the CCU 11201 via the transmission cable 11400.

Furthermore, the communication unit 11404 receives a control signal for controlling driving of the camera head 11102 from the CCU 11201, and supplies the control signal to the camera head control unit 11405. The control signal includes, for example, information regarding imaging conditions such as information for specifying a frame rate of the captured image, information for specifying an exposure value at the time of imaging, and/or information for specifying the magnification and the focal point of the captured image.

Note that the imaging conditions such as the frame rate, the exposure value, the magnification, and the focal point may be appropriately specified by the user, or may be automatically set by the control unit 11413 of the CCU 11201 on the basis of the acquired image signal. In the latter case, the endoscope 11100 has a so-called auto exposure (AE) function, an auto focus (AF) function, and an auto white balance (AWB) function.

The camera head control unit 11405 controls the driving of the camera head 11102 on the basis of the control signal received from the CCU 11201 via the communication unit 11404.

The communication unit 11411 is implemented by a communication device for transmitting and receiving various types of information to and from the camera head 11102. The communication unit 11411 receives the image signal transmitted from the camera head 11102 via the transmission cable 11400.

Furthermore, the communication unit 11411 transmits a control signal for controlling the driving of the camera head 11102 to the camera head 11102. The image signal or the control signal can be transmitted by electric communication, optical communication, or the like.

The image processing unit 11412 performs various types of image processing on the image signal that is raw data transmitted from the camera head 11102.

The control unit 11413 performs various types of controls related to capturing of the image of the surgical site or the like performed by the endoscope 11100 and display of the captured image obtained by the capturing of the image of the surgical site or the like. For example, the control unit 11413 generates a control signal for controlling the driving of the camera head 11102.

Furthermore, the control unit 11413 causes the display device 11202 to display the captured image of the surgical site or the like on the basis of the image signal subjected to the image processing by the image processing unit 11412. At this time, the control unit 11413 may recognize various objects in the captured image by using various image recognition technologies. For example, the control unit 11413 can recognize a surgical tool such as forceps, a specific site in the living body, bleeding, mist at the time of using the energy treatment tool 11112, and the like by detecting an edge shape, color, and the like of the object included in the captured image. When displaying the captured image on the display device 11202, the control unit 11413 may superimpose various types of surgery support information on the image of the surgical site by using the recognition result. The surgery support information is superimposed and displayed and presented to the operator 11131, such that a burden on the operator 11131 can be reduced and the operator 11131 can reliably proceed with the surgery.

The transmission cable 11400 connecting the camera head 11102 and the CCU 11201 is an electric signal cable supporting electric signal communication, an optical fiber supporting optical communication, or a composite cable thereof.

Here, in the example of FIG. 33, wired communication is performed using the transmission cable 11400, but wireless communication may be performed between the camera head 11102 and the CCU 11201.

Hereinabove, an example of the endoscopic surgery system to which the technology according to the present disclosure can be applied has been described. The technology according to the present disclosure can be applied to, for example, the CCU 11201 among the above-described configurations. Specifically, the above-described control units 220, 220B, and 220C can be applied to the image processing unit 11412. By applying the technology according to the present disclosure to the image processing unit 11412, it is possible to measure a shape of a surface in a body from an in-vivo image captured by the endoscope 11100.

Note that, here, the endoscopic surgery system has been described as an example, but the technology according to the present disclosure may be applied to, for example, a microscopic surgery system or the like.

14. Supplementary Description

As described above, the preferred embodiments of the present disclosure have been described in detail with reference to the accompanying drawings, but the technical scope of the present disclosure is not limited to such examples. It will be apparent to those skilled in the art to which the present disclosure pertains that various modifications or alterations can be conceived within the scope of the technical idea described in the claims and it is naturally understood that these modifications or alterations fall within the technical scope of the present disclosure.

Further, among the respective processing described in the above-described embodiment, all or some of the processing described as being automatically performed can be manually performed. Alternatively, all or some of the processing described as being manually performed can be automatically performed by a known method. In addition, the processing procedures, specific names, information including various data and parameters illustrated in the specification and drawings can be arbitrarily changed unless otherwise specified. For example, various information illustrated in each drawing is not limited to the illustrated information.

Further, each illustrated component of each device is functionally conceptual, and does not necessarily have to be configured physically as illustrated in the drawings. That is, the specific modes of distribution/integration of the respective devices are not limited to those illustrated in the drawings. All or some of the devices can be functionally or physically distributed/integrated in any arbitrary unit, depending on various loads or the status of use.

In addition, the above-described embodiments and modified example can be appropriately combined as long as the processing contents do not contradict each other. Furthermore, in the above-described embodiments, a microscope has been described as an example of the image processing device, but the image processing of the present disclosure is also applicable to an imaging device other than the microscope.

Furthermore, the effects described in the present specification are merely illustrative or exemplary and are not restrictive. That is, the technology according to the present disclosure can exhibit, in addition to or in place of the above-described effects, other effects obvious to those skilled in the art from the description of the present specification.

Note that the following configurations also fall within the technical scope of the present disclosure.

(1)

An information processing device comprising: a control unit that acquires a captured image of a target imaged by a sensor, extracts a flat region from the captured image based on a luminance value of the captured image, and calculates shape information regarding a shape of a surface of the target based on information regarding the sensor and the flat region of the captured image, wherein the captured image is an image obtained from reflected light of light emitted to the target from a plurality of light sources arranged at different positions, respectively.

(2)

The information processing device according to (1), wherein the control unit acquires the captured image obtained from the reflected light of the light simultaneously emitted to the target from the plurality of light sources.

(3)

The information processing device according to (1) or (2), wherein the control unit sets, as the flat region, a region in which the luminance value of the captured image is equal to or more than a predetermined threshold.

(4)

The information processing device according to (1), wherein the control unit acquires, for each light source, the captured image obtained from the reflected light of the light emitted to the target from one of the plurality of light sources, and extracts, as the flat region, a region in which a change in luminance value between the plurality of captured images acquired for each light source is smaller than a predetermined threshold.

(5)

The information processing device according to any one of (1) to (4), wherein the control unit generates a smoothing image by performing smoothing processing on the captured image, and extracts the flat region from the captured image based on the smoothing image.

(6)

The information processing device according to any one of (1) to (5), wherein the control unit divides the captured image into a plurality of divided regions, and extracts the flat region for each of the plurality of divided regions to calculate the shape information.

(7)

The information processing device according to any one of (1) to (6), wherein the control unit calculates normal information of the flat region in the captured image, and inputs the normal information to a model generated by machine learning to obtain the shape information.

(8)

The information processing device according to (7), wherein the model is generated by updating a weight based on a result of comparison between a plurality of correct answer candidate images and output data of the model, and the plurality of correct answer candidate images are generated by shifting a correct answer image by different numbers of pixels, respectively.

(9)

The information processing device according to (8), wherein the model calculates a least square error between each of the plurality of correct answer candidate images and the output data, and is generated by updating the weight based on a minimum value of a plurality of the least squares errors.

(10)
The information processing device according to (1), wherein the control unit extracts the flat region based on a contrast value calculated from the luminance value of the captured image.

(11)
The information processing device according to (1), wherein the control unit divides the captured image into a plurality of divided regions, calculates the contrast value for each of the plurality of divided regions, and determines whether or not the divided region is flat based on the contrast value to extract the flat region.

(12)
The information processing device according to (10) or (11), wherein the control unit acquires a plurality of the captured images whose depth-of-field planes of the sensor are different from each other, and extracts the flat region from each of the plurality of captured images.

(13)
An information processing method comprising:
acquiring a captured image of a target imaged by a sensor;
extracting a flat region from the captured image based on a luminance value of the captured image; and
calculating shape information regarding a shape of a surface of the target based on information regarding the sensor and the flat region of the captured image,
wherein the captured image is an image obtained from reflected light of light emitted to the target from a plurality of light sources arranged at different positions, respectively.

REFERENCE SIGNS LIST

10 HEAD-MOUNTED PORTION
100 MICROSCOPE
150 SENSOR
160 POINT LIGHT SOURCE
200 INFORMATION PROCESSING DEVICE
220 CONTROL UNIT
221 ACQUISITION UNIT
222 NORMAL CALCULATION UNIT
223 DEPTH CALCULATION UNIT
224 DISPLAY CONTROL UNIT
225 REGION ACQUISITION UNIT
226 NORMAL FREQUENCY SEPARATION UNIT
227 DEPTH COMBINATION UNIT
230 STORAGE UNIT

The invention claimed is:
1. An information processing device, comprising:
a central processing unit (CPU) configured to:
acquire a captured image of a target from a sensor, wherein
the captured image is based on reflected light of light emitted to the target from a plurality of light sources, and
each light source of the plurality of light sources is at a different position;
extract a flat region from the captured image based on a luminance value of the captured image;
acquire information regarding the sensor; and
calculate shape information regarding a shape of a surface of the target, based on the flat region and the information regarding the sensor.

2. The information processing device according to claim 1, wherein the light is simultaneously emitted to the target from the plurality of light sources.

3. The information processing device according to claim 2, wherein the CPU is further configured to set, as the flat region, a region in which the luminance value of the captured image is equal to or more than a threshold.

4. The information processing device according to claim 2, wherein the CPU is further configured to:
perform a smoothing process on the captured image;
generate a smoothing image based on the smoothing process on the captured image; and
extract the flat region from the captured image based on the smoothing image.

5. The information processing device according to claim 4, wherein the CPU is further configured to:
divide the captured image into a plurality of divided regions; and
extract the flat region for each divided region of the plurality of divided regions to calculate the shape information.

6. The information processing device according to claim 5, wherein the CPU is further configured to:
calculate normal information of the flat region in the captured image; and
input the normal information to a machine learning model by to calculate the shape information.

7. The information processing device according to claim 6, wherein the CPU is further configured to:
generate the machine learning model;
generate a correct answer candidate image by shift of a correct answer image by a specific number of pixels;
compare the correct answer candidate image with output data of the machine leaning model; and
update a weight associated with the machine learning model, based on a result of the comparison between the correct answer candidate image and the output data.

8. The information processing device according to claim 7, wherein the CPU is further configured to:
calculate, based on the machine learning model, a least square error between the correct answer candidate image and the output data; and
update the weight based on the least square error.

9. The information processing device according to claim 1, wherein the CPU is further configured to:
acquire a plurality of captured images of the target from the sensor,
wherein the plurality of captured images includes the captured image; and
extracts, as the flat region, a region in which a change in luminance value between the plurality of captured images is smaller than a threshold.

10. The information processing device according to claim 1, wherein the CPU is further configured to:
calculate a contrast value based on the luminance value of the captured image; and
extract the flat region based on the contrast value.

11. The information processing device according to claim 10, wherein the CPU is further configured to:
divide the captured image into a plurality of divided regions;
calculate the contrast value for each divided region of the plurality of divided regions;
determine, based on the contrast value, a divided region of the plurality of divided regions is flat; and
extract the flat region based the determination that the divided region is flat.

12. The information processing device according to claim 10, wherein the CPU is further configured to:
acquire a plurality of captured images, wherein
each captured image of the plurality of captured images has a different depth-of-field plane of the sensor, and
the plurality of captured images includes the captured image; and
extract the flat region from each captured image of the plurality of captured images.

13. An information processing method, comprising:
acquiring a captured image of a target from a sensor, wherein
the captured image is based on reflected light of light emitted to the target from a plurality of light sources, and
each light source of the plurality of light sources is at a different position;
extracting a flat region from the captured image based on a luminance value of the captured image;
acquiring information regarding the sensor; and
calculating shape information regarding a shape of a surface of the target, based on the flat region and the information regarding the sensor.

* * * * *